United States Patent
Nagata et al.

(10) Patent No.: US 7,715,520 B2
(45) Date of Patent: May 11, 2010

(54) X-RAY COMPUTED TOMOGRAPHY APPARATUS

(75) Inventors: Kiyoshi Nagata, Otawara (JP); Masaharu Tsuyuki, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 114 days.

(21) Appl. No.: 11/470,928

(22) Filed: Sep. 7, 2006

(65) Prior Publication Data

US 2007/0053483 A1 Mar. 8, 2007

(30) Foreign Application Priority Data

Sep. 7, 2005 (JP) ............................. 2005-259614
Sep. 30, 2005 (JP) ............................. 2005-285863

(51) Int. Cl.
*H05G 1/62* (2006.01)
*G01N 23/083* (2006.01)

(52) U.S. Cl. .................... 378/8; 378/16; 378/95
(58) Field of Classification Search .......... 378/8, 378/16, 95; 600/428
See application file for complete search history.

(56) References Cited

U.S. PATENT DOCUMENTS

| | | | |
|---|---|---|---|
| 6,298,111 B1 | 10/2001 | Ozaki | |
| 6,370,217 B1 | 4/2002 | Hu et al. | |
| 6,504,893 B1 | 1/2003 | Flohr et al. | |
| 6,708,052 B1 * | 3/2004 | Mao et al. | 600/407 |
| 6,836,529 B2 * | 12/2004 | Li et al. | 378/8 |
| 7,251,308 B2 * | 7/2007 | Tsuyuki | 378/8 |
| 2004/0120446 A1 | 6/2004 | Londt et al. | |

(Continued)

FOREIGN PATENT DOCUMENTS

EP 1 090 586 A2 4/2001

(Continued)

OTHER PUBLICATIONS

Marc Kachelriess, et al., "ECG-correlated image reconstruction from subsecond multi-slice spiral CT scans of the heart", Medical Physics, vol. 27, No. 8, Am. Assoc. Phys. Med., XP012011239, Aug. 1, 2000, pp. 1881-1902.

(Continued)

*Primary Examiner*—Irakli Kiknadze
*Assistant Examiner*—Thomas R Artman
(74) *Attorney, Agent, or Firm*—Oblon, Spivak, McClelland, Maier & Neustadt, L.L.P.

(57) ABSTRACT

An X-ray computed tomography apparatus includes an X-ray source, a high voltage generating unit, an X-ray detector detecting X-rays transmitted through a subject to generate projection data, a storage unit storing the projection data in association with electrocardiographic data of the subject, a setting unit setting a specific cardiac phase in accordance with an operator's instruction, a reconstruction unit reconstructing a tomogram based on projection data sets acquired in specific periods centered on the specific cardiac phase throughout cardiac cycles, a period extending unit extending the specific period on the basis of a heart rate fluctuation range of the subject, and a control unit controlling the high voltage generating unit to generate a relatively high dose of X-rays in the extended specific period and generate a relatively low dose of X-rays in a period other than the extended specific period.

49 Claims, 11 Drawing Sheets

U.S. PATENT DOCUMENTS

| | | | |
|---|---|---|---|
| 2005/0101858 A1* | 5/2005 | Flohr et al. | 600/425 |
| 2005/0111623 A1 | 5/2005 | Bruder et al. | |
| 2005/0238138 A1* | 10/2005 | Imai | 378/95 |
| 2007/0086562 A1* | 4/2007 | Manzke et al. | 378/8 |

FOREIGN PATENT DOCUMENTS

| | | |
|---|---|---|
| EP | 1 090 586 A3 | 4/2001 |
| JP | 2000-51208 | 2/2000 |
| JP | 2000-342577 | 12/2000 |
| WO | WO 01/43642 | 6/2001 |
| WO | WO 2004/075115 A1 | 9/2004 |

OTHER PUBLICATIONS

M. Grass, et al., "Helical cardiac cone beam reconstruction using retrospective ECG gating", Institute of Physics Publishing, Physics in Medicine and Biology, vol. 48, No. 18, XP-002286729, Sep. 3, 2003, pp. 3069-3084.

* cited by examiner

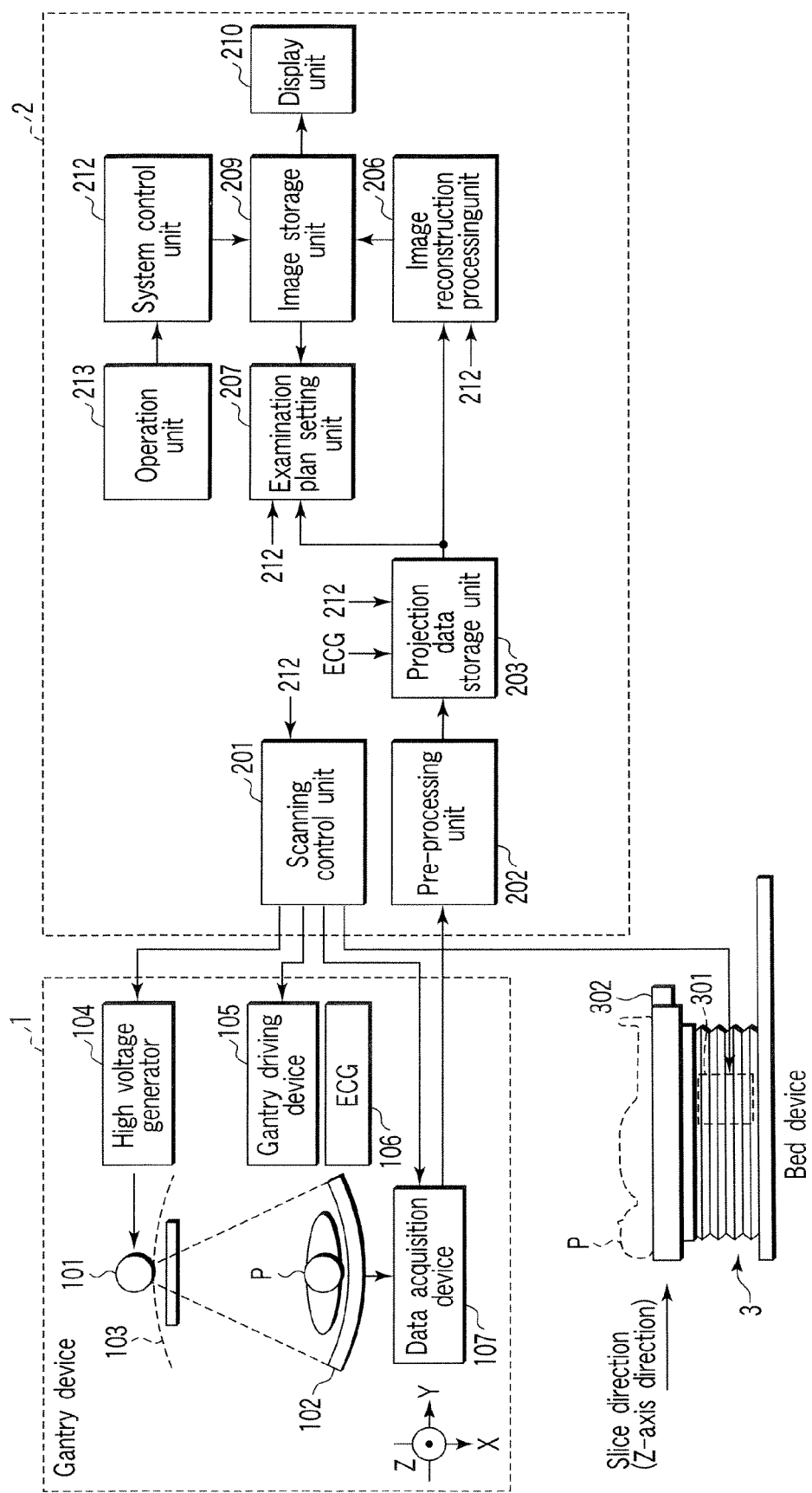
F I G. 1

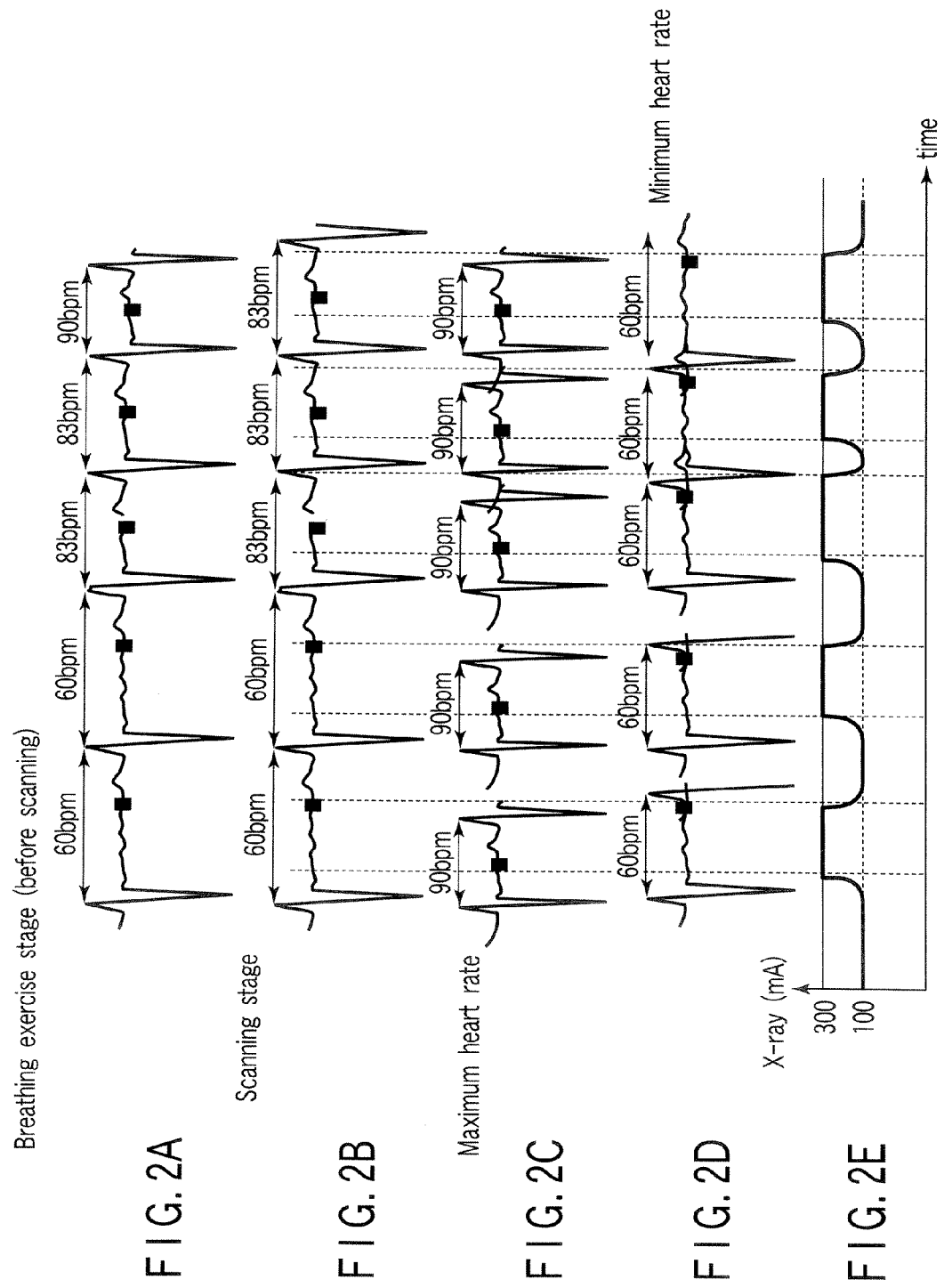

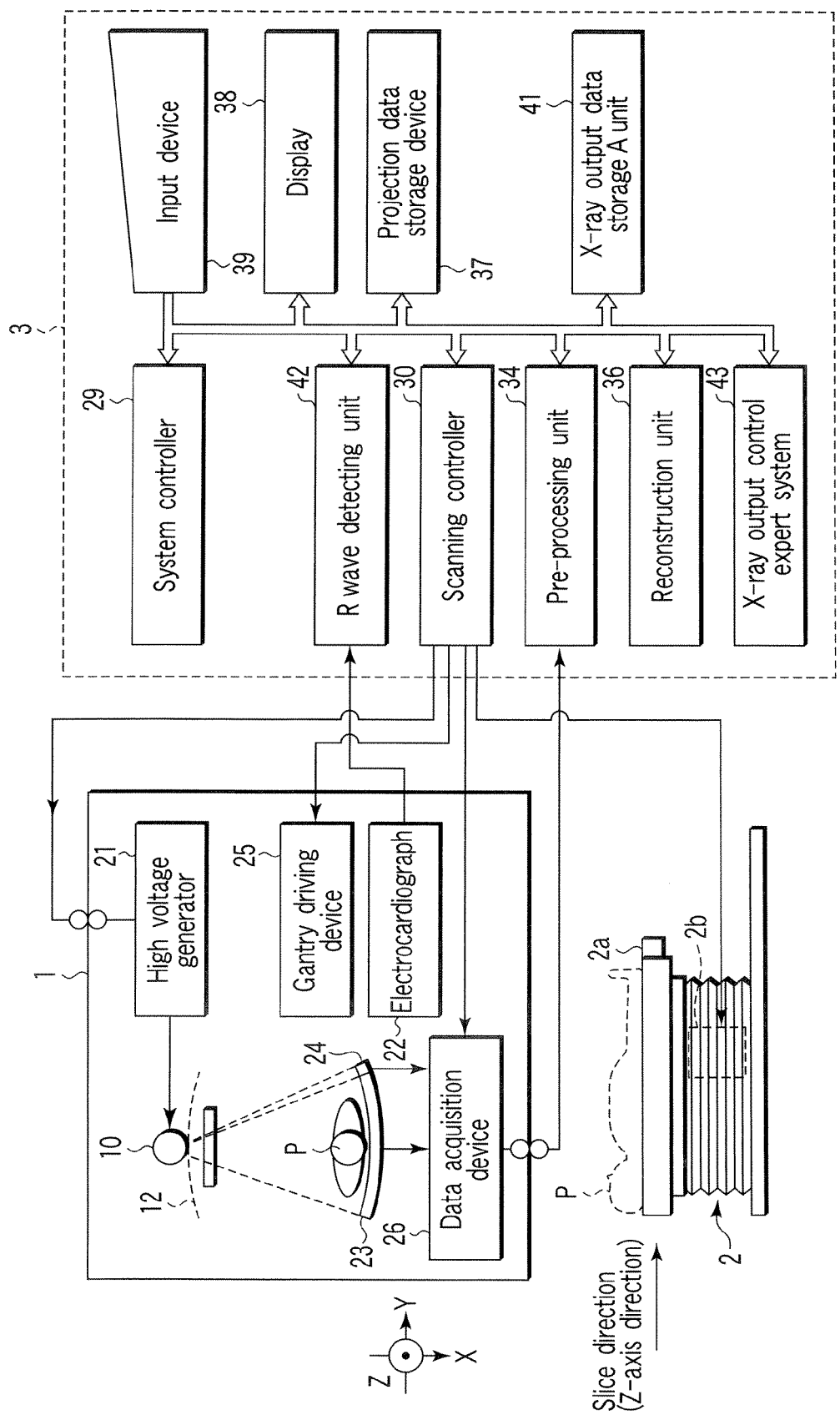
F I G. 5

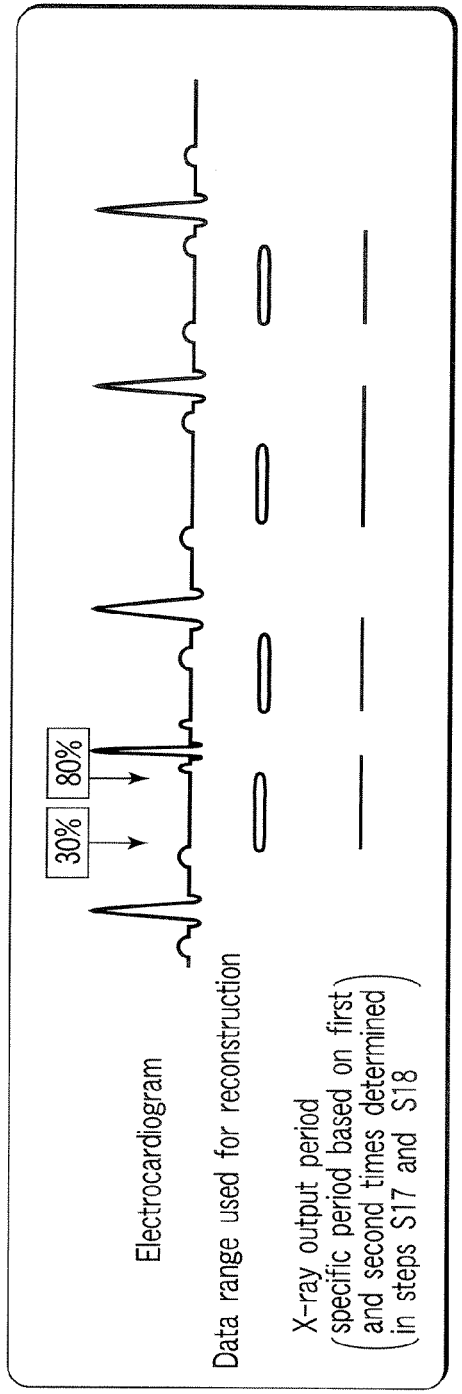
F I G. 9
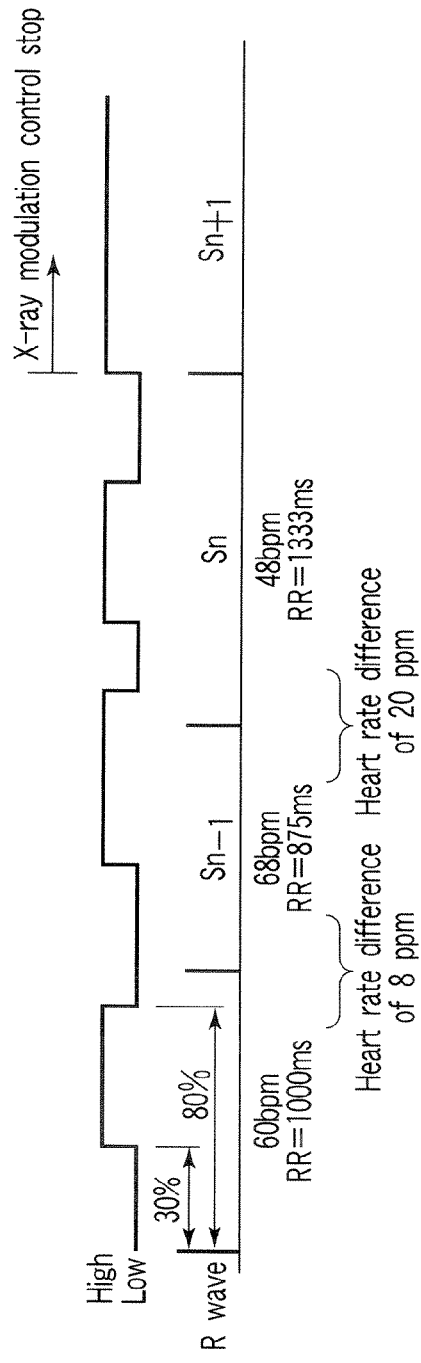
F I G. 10

X-RAY COMPUTED TOMOGRAPHY APPARATUS

CROSS-REFERENCE TO RELATED APPLICATIONS

This application is based upon and claims the benefit of priority from prior Japanese Patent Applications No. 2005-259614, filed Sep. 7, 2005; and No. 2005-285863, filed Sep. 30, 2005, the entire contents of both of which are incorporated herein by reference.

BACKGROUND OF THE INVENTION

1. Field of the Invention

The present invention relates to an X-ray computed tomography apparatus which can perform ECG gated reconstruction.

2. Description of the Related Art

An X-ray computed tomography apparatus provides information about a subject to be examined in the form of images on the basis of the intensities of X-rays transmitted through the subject, and serves as an important role in many medical activities such as disease diagnosis, medical treatment, and surgical operation planning.

In examination of the heart which moves fast, ECG gated scanning is performed. ECG gated scanning is performed to acquire ECG gated signals (trigger signals and R wave signals) and electrocardiographic signals (ECG signals) in parallel with scanning and obtain an image synchronous with a cardiac phase by using the electrocardiographic waveform signals or the like after data acquisition.

Recent cardiac examination attempts to reduce exposure by applying X-rays only in a specific phase by using electrocardiographic information.

According to Jpn. Pat. Appln. KOKAI Publication No. 2000-342577, there is no description about how an X-ray application period is determined. According to Jpn. Pat. Appln. KOKAI Publication No. 2000-51208, an X-ray application period at the time of scanning is determined by using an R-R wave interval (cardiac cycle) corresponding to one heartbeat which is acquired before scanning. This technique may be applicable to a heart phantom with a constant cardiac cycle. However, the actual cardiac cycle of a subject (patient) is unstable, and a cardiac cycle corresponding to several heartbeats is not constant even before scanning. It is therefore not practical to determine an X-ray application period by using only a cardiac cycle corresponding to one heartbeat. In cardiac examination which is performed for several to several ten seconds, all a plurality of cardiac cycles at the time of scanning are not completely equal to one cardiac cycle before the scanning. For this reason, it may happen that no X-rays are applied (no data can be obtained) in a phase which the operator wants to reconstruct, and data in an unnecessary period is acquired.

As described above, an X-ray computed tomography apparatus provides information about a subject to be examined in the form of images on the basis of the intensities of X-rays transmitted through the subject, and serves as an important role in many medical activities such as disease diagnosis, medical treatment, and surgical operation planning. In examination of a fast-moving part using an X-ray computed tomography apparatus, and in particular, cardiac examination, one of the important challenges is to improve the time resolution of images. A direct method of achieving this challenge is to shorten the time taken for one rotation of an X-ray tube, i.e., to speed up scanning. Speeding up scanning makes a so-called ECG gated scanning method effectively function, which acquires only data in a specific period in a cardiac cycle by performing scanning in synchronism with an electrocardiogram. X-ray are generated only in a specific period or the intensity of X-rays is increased in a specific period. This makes it possible to reduce an exposure dose as compared with a case wherein X-rays are continuously applied.

However, arrhythmia or the like sometimes causes a situation in which projection data necessary for image reconstruction in a desired cardiac time phase has not been acquired, or projection data has not been acquired with a high S/N ratio. In such a situation, the image quality of a reconstructed image deteriorates. In some case, re-scanning is required. Furthermore, there is no means to check the above situation before reconstruction.

BRIEF SUMMARY OF THE INVENTION

It is an object of the present invention to prevent the omission of part of projection data required for image reconstruction in an X-ray computed tomography apparatus which can perform ECG gated reconstruction.

According to a first aspect of the present invention, there is provided an X-ray computed tomography apparatus comprising an X-ray source which generates X-rays, an X-ray detector which detects X-rays transmitted through a subject to be examined to generate projection data, a storage unit which stores the projection data in association with electrocardiographic data of the subject, a setting unit which sets a specific cardiac phase in accordance with an operator's instruction, a reconstruction unit which reconstructs an image on the basis of a plurality of projection data sets acquired in a plurality of specific periods throughout a plurality of cardiac cycles, a determining unit which determines a first period in which the subject is scanned by high dose of X-ray based on the specific cardiac phase and a heart rate fluctuation range of the subject; and a control unit which controls a tube current of the X-ray source to generate a relatively high dose of X-rays in the first period and generate a relatively low dose of X-rays or stop a generation of X-rays in a second period other than the first period.

According to a second aspect of the present invention, there is provided an X-ray computed tomography apparatus comprising a storage unit which stores electrocardiographic information acquired from a subject to be examined, a setting unit which sets a cardiac cycle of the subject which is to be reconstructed, an X-ray source which applies X-rays to the subject, a high voltage generating unit which applies a high voltage to the X-ray source, an X-ray detector which detects X-rays transmitted through the subject, a reconstruction unit which reconstructs an image of a cardiac phase set by the setting unit on the basis of projection data detected by the detector, and a control unit which controls a tube current of the X-ray source to scan in the cardiac to scan in the cardiac phase range set by the setting unit at a high X-ray dose and scan at a low X-ray dose or stop a generation of X-rays in a range obtained by excluding the cardiac phase range, from the electrocardiographic cycle in response to an electrocardiogram as a trigger which is obtained in parallel with the scanning.

According to a third aspect of the present invention, there is provided an X-ray computed tomography apparatus comprising a gantry which includes an X-ray source which applies X-rays to a subject to be examined and an X-ray detector which detects X-rays transmitted through the subject, and scans the subject, a storage unit which stores an electrocardiogram acquired from the subject, a setting unit which sets a cardiac phase in which a tomogram of the subject is reconstructed, a reconstruction unit which reconstructs a tomogram of a specific phase in a cardiac phase range set by the setting unit on the basis of projection data detected by the detector and a control unit which controls a tube current of the X-ray source to scan in the cardiac phase range set by the setting unit at a high X-ray dose and scan at a low X-ray dose or stop a generation of X-rays in a range obtained by excluding the cardiac phase range, from the electrocardiographic cycle in response to an electrocardiogram as a trigger which is obtained in parallel with the scanning.

According to a fourth aspect of the present invention, there is provided an X-ray computed tomography apparatus comprising a scanning unit which performs helical scanning while modulating a X-ray dose, a reconstruction unit which sequentially reconstructs tomograms by fan beam reconstruction on the basis of projection data in parallel with the helical scanning, and reconstructs an image by cone beam reconstruction on the basis of projection data after the end of the helical scanning, and a display unit which displays tomograms sequentially reconstructed by using the fan beam reconstruction in parallel with the helical scanning, and displays an image reconstructed by using the cone beam reconstruction after the end of the helical scanning.

According to a fifth aspect of the present invention, there is provided an X-ray computed tomography apparatus comprising a scanning unit which includes an X-ray source which applies X-rays to a subject to be examined and an X-ray detector which detects X-rays transmitted through the subject, and scans the subject, a storage unit which stores an electrocardiogram acquired from the subject in parallel with the scanning, a setting unit which sets a cardiac phase in which an image of the subject is reconstructed, a reconstruction unit which reconstructs an image of a cardiac phase set by the setting unit on the basis of projection data detected by the detector, and a control unit which controls a tube current of the X-ray source to increase an X-ray dose in a predetermined range including a cardiac phase set by the setting unit and decrease an X-ray dose in a range excluding the predetermined range on the basis of an electrocardiogram acquired in parallel with the scanning.

According to a sixth aspect of the present invention, there is provided an X-ray computed tomography apparatus comprising a scanning unit which includes an X-ray source which applies X-rays to a subject to be examined and an X-ray detector which detects X-rays transmitted through the subject, and scans the subject, a storage unit which stores electrocardiographic information acquired from the subject before the scanning and in parallel with the scanning, a setting unit which sets a cardiac phase in which an image of the subject is to be reconstructed, a reconstruction unit which reconstructs an image of a cardiac phase set by the setting unit on the basis of projection data detected by the detector, and a control unit which controls a tube current of the X-ray source to increase an X-ray dose in a predetermined range determined on the basis of a plurality of heart rates acquired before the scanning which are stored in the storage unit and decrease an X-ray dose in a range excluding the predetermined range in response to electrocardiographic information as a trigger which is obtained in parallel with the scanning and stored in the storage unit.

According to a seventh aspect of the present invention, there is provided an X-ray computed tomography apparatus comprising an X-ray source which generates X-rays, an X-ray detector which detects X-rays transmitted through a subject to be examined to generate projection data, a storage unit which stores the projection data in association with electrocardiographic data of the subject, an addition processing unit which weights and adds projection data with the same view between a plurality of projection data sets acquired in a plurality of specific periods centered on a specific cardiac phase throughout a plurality of cardiac cycles, and a reconstruction unit which reconstructs an image on the basis of the plurality of weighted and added projection data sets.

According to an eighth aspect of the present invention, there is provided an X-ray computed tomography apparatus comprising an X-ray source which generates X-rays, an X-ray detector which detects X-rays transmitted through a subject to generate projection data, a specific period setting unit which sets a specific period in a cardiac cycle of the subject in accordance with an operator's instruction, a reconstruction unit which reconstructs an image on the basis of projection data acquired in the specific period, an extension processing unit which extends the specific period on the basis of a time width corresponding to an angle range of projection data required for image reconstruction, and a control unit which controls generation/stop or intensity modulation of X-rays from the X-ray tube in accordance with the extended specific period.

According to a ninth aspect of the present invention, there is provided an X-ray computed tomography apparatus comprising an X-ray source which generates X-rays, an X-ray detector which detects X-rays transmitted through a subject to be examined to generate projection data, a storage unit which stores the projection data in association with electrocardiographic data of the subject; a setting unit which sets a specific cardiac phase in accordance with an operator's instruction, a reconstruction unit which reconstructs an image on the basis of a plurality of projection data sets acquired in a plurality of specific periods throughout a plurality of cardiac cycles, the specific periods corresponding the specific cardiac phase, a period extending unit which extends each of the specific periods on the basis of a heart rate fluctuation range of the subject, and a control unit which controls a tube current of the X-ray source to generate a relatively high dose of X-rays and generate a relatively low dose of X-rays or stop a generation of X-rays in a period other than the extended specific period. Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray computed tomography apparatus according to the first embodiment of the present invention;

FIG. 2A is a diagram showing a temporal change in heart rate at the time of exercise according to the first embodiment;

FIG. 2B is a diagram showing a temporal change in heart rate at the time of scanning according to the first embodiment;

FIG. 2C is a diagram showing the position of each cardiac phase with reference to the maximum heart rate at the time of exercise on the temporal change in heart rate in FIG. 2B;

FIG. 2D is a diagram showing the position of each cardiac phase with reference to the minimum heart rate at the time of exercise on the temporal change in heart rate in FIG. 2B;

FIG. 2E is a diagram showing a high X-ray dose period in this embodiment;

FIG. 5 is a block diagram showing the arrangement of an X-ray computed tomography apparatus according to an embodiment of the present invention;

FIG. 9 is a diagram showing an example of a window during scanning which is provided by an X-ray output control expert system in FIG. 5;

FIG. 10 is a timing chart showing X-ray modulation control stopping operation to be performed when a heart rate difference exceeds an upper limit heart rate difference in step S22 in FIG. 7.

DETAILED DESCRIPTION OF THE INVENTION

First Embodiment

Figure 3A:
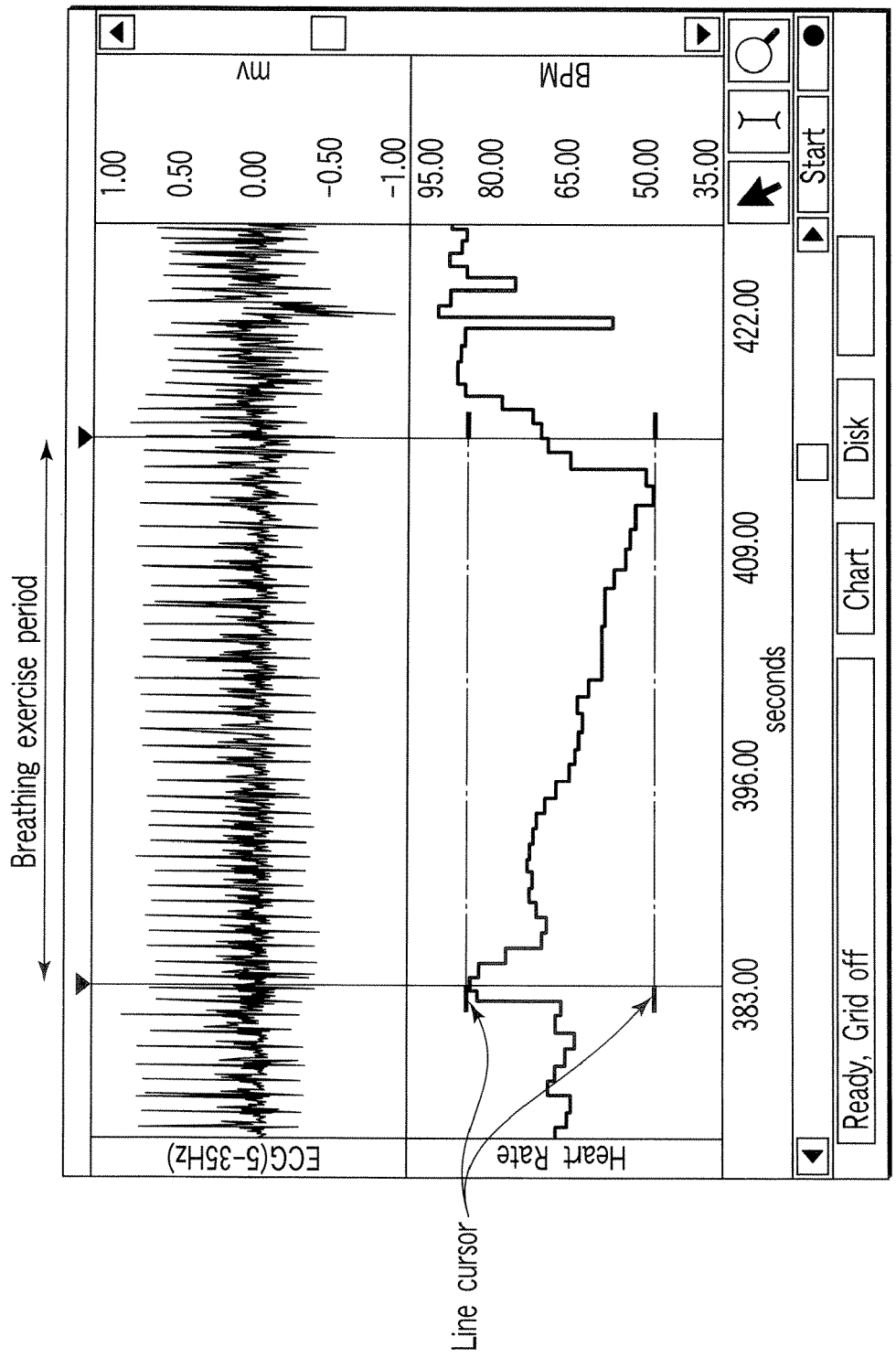
FIG. 3A is a diagram showing a heart rate fluctuation range manually set through an operation unit in FIG. 1.

The first embodiment of an X-ray computed tomography apparatus according to the present invention will be described below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements are arrayed in the form of a ring or plane, and only an X-ray tube rotates around a subject to be examined. The present invention can be applied to either type. In this case, the rotate/rotate type, which is currently the mainstream, will be exemplified. In order to reconstruct one-slice tomogram data, projection data corresponding to one rotation around a subject to be examined, i.e., about 360°, is required (full reconstruction method), or projection data corresponding to 180°+α (α: fan angle) is required in the half reconstruction method. This embodiment uses the half reconstruction method effective for imaging the heart with fast movement or the like.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. In this case, the former type, i.e., the indirect conversion type, will be exemplified. The present invention can be applied to both a single-tube type X-ray computed tomography apparatus and a multi-tube type X-ray computed tomography apparatus. The single-tube type X-ray computed tomography apparatus will be exemplified here.

FIG. 1 shows the schematic arrangement of the X-ray computed tomography apparatus according to this embodiment. This X-ray computed tomography apparatus comprises a gantry device (scanning unit) 1 which acquires projection data associated with a subject (patient) P, a bed device 3 on which the subject P is placed, and a console 2 which controls the gantry device 1 and the bed device 3 and performs image reconstruction processing, image display, and the like based on the data acquired by the gantry device 1.

The gantry device 1 comprises a housing accommodating an X-ray tube 101, X-ray detector 102, rotating frame 103, high voltage generator 104, gantry driving device 105, and data acquisition device 107. The housing has an opening portion for diagnosis in which the subject P is inserted. The X-ray tube 101 and the X-ray detector 102 are mounted on the ring-like rotating frame 103 which is rotated/driven by the gantry driving device 105. In this case, the rotation axis of the rotating frame 103 is defined as the Z-axis. In a rotating coordinate system centered on the Z-axis, an axis perpendicular to the Z-axis which connects the focal point of the X-ray tube 101 and the center of the detection surface of the X-ray detector 102 is defined as the X-axis. The Y-axis is perpendicular to both the Z-axis and the X-axis.

The rotating frame 103 is rotated by the gantry driving device 105 under the control of a scanning control unit 201. Upon rotation of the rotating frame 103, the X-ray tube 101 and the X-ray detector 102 rotate around the subject P. When a high voltage is applied from the high voltage generator 104 to the X-ray tube 101 under the control of the scanning control unit 201, the X-ray tube 101 generates X-rays. The X-rays generated from the X-ray tube 101 and transmitted through the subject are detected by the X-ray detector 102 and are acquired as projection data by the data acquisition device 107. A top 302 of the bed device 3 is moved by a bed driving device 301. The scanning control unit 201 controls the rotation of the rotating frame 103 and the movement of the top 302. This control allows the top 302 to make continuous movement synchronously during constant rotation of the rotating frame 103. This makes it possible to realize so-called helical scanning of moving the X-ray tube 101 (X-ray source) helically relative to the subject P and acquiring projection data at a plurality of positions on the helical path.

This embodiment will exemplify a case wherein projection data obtained by multi-helical scanning which is a technique of simultaneously acquiring data by using a multi-row detector. However, this embodiment is also applicable to so-called dynamic scanning of continuously acquiring projection data while the top 302 is at rest or conventional scanning of repeating the operation of acquiring projection data corresponding to one rotation while the top 302 is at rest at a given position and acquiring projection data corresponding to one rotation at the next position after the top 302 is moved and stopped.

The rotating frame 103 has an opening portion in its central portion like the housing. When scanning is to be performed, the subject P placed on the top 302 of the bed device 3 is inserted into the opening portion. An electrocardiograph 106 serves to detect an electrocardiographic signal from an electrode attached to the subject P. The electrocardiograph 106 detects a weak current generated from the heart of the subject P and outputs a temporal change in detected current as an electrocardiogram. Note that this embodiment, as will be described later, a system control unit 212 obtains a heart rate on the basis of the electrocardiographic information (P wave, Q wave, R wave, S wave, or T wave; R wave in this embodiment) obtained by the electrocardiograph 106. However, the electrocardiograph 106 may acquire electrocardiographic information, and the system control unit 212 may obtain an electrocardiogram and a heart rate. FIG. 1 shows the electrocardiograph 106 as part of the gantry device 1. However, the electrocardiograph 106 may be configured independently of the gantry device 1, and it suffices to have a function of acquiring electrocardiographic information or electrocardiographic signals from the electrocardiograph 106 and a function of storing the electrocardiographic signals in a storage unit such as a projection data storage unit 203.

The high voltage generator 104 applies a tube voltage between the cathode and anode of the X-ray tube 101. The high voltage generator 104 also supplies a filament current (tube current) to the filament of the X-ray tube 101. X-rays are generated from the target of the anode of the X-ray tube 101 by the application of the tube voltage and the supply of the filament current.

The X-ray detector 102 is used to detect X-rays transmitted through the subject P. As the X-ray detector 102, a multi-slice type detector or a single-slice type detector may be used. In this case, the X-ray detector 102 will be described as a multi-slice type detector which exhibits a high exposure reducing effect than an X-ray modulation function (to be described later). The X-ray detector 102 is provided with pluralities of detection elements for detecting X-rays which are arranged in the channel direction (approximated to the Y-axis direction) and the slice direction (Z-axis direction) of the subject, respectively. For example, a plurality of X-ray detection elements, e.g., about 600 to 1,000 detection elements, are arranged in the channel direction, and about 24 to 256 rows of detection elements are arranged side by side in the slice direction. In this embodiment, a multi-row detector is used, in which a plurality of X-ray detection elements each having a 0.5 mm×0.5 mm square light-receiving surface are arranged such that 1,000 elements are arranged in the channel direction, and 64 rows of elements are arranged in the slice direction. Each detection element includes a scintillator and a photodiode chip (not shown). The X-ray detector 102 may either be a multi-slice type detector having detection elements with an equal size arranged in the slice direction or a multi-slice type detector having a plurality of detection elements with different sizes arranged in the slice direction at uneven pitches.

A data acquisition device (DAS (Data Acquisition System)) 107 converts a signal output from the X-ray detector 102 for each channel into a voltage signal, amplifies it, and further converts it into a digital signal. This data (also called pure raw data) is supplied to the console 2 placed outside the gantry device 1. A pre-processing unit 202 of the console 2 performs correction processing such as offset correction, reference correction, and sensitivity correction for the data (pure raw data) output from the data acquisition device 107. The pre-processed pure raw data is generally called raw data. In this case, pure raw data and raw data will be genetically called "projection data".

Projection data is stored in the projection data storage unit 203 of the console 2, together with the electrocardiographic data obtained by the electrocardiograph 106, while codes representing a view representing the rotation angle of the X-ray tube 101 at the time of data acquisition, a channel number, and a row number (the position of the top 302 in some case) are associated with each other. The projection data and the electrocardiographic signal (or electrocardiographic information) are associated with each other (or synchronized with each other according to a person skilled in the art). The projection data and the electrocardiographic signal may be stored physically or individually stored in one or more storage media. Alternatively, one storage medium may have different storage areas for the projection data and the electrocardiographic signal.

The console 2 includes the scanning control unit 201, an image reconstruction processing unit 206, an examination plan setting unit 207, an image storage unit 209, a display unit 210, and the system control unit 212 in addition to the pre-processing unit 202 and the projection data storage unit 203.

The image reconstruction processing unit 206 performs ECG gated reconstruction on the basis of the electrocardiographic signal (or the heart rate obtained by the system control unit 212) and projection data stored in the projection data storage unit 203. The image reconstruction processing unit 206 comprises a half reconstruction function as an ECG gated reconstruction function and a segment reconstruction function.

In half reconstruction, the X-ray tube requires a projection data group which covers the range of 180°+α (where α is the fan angle of a fan-shaped X-ray beam). In the segment reconstruction method, a projection data group comprises a plurality of projection data sets (also referred to as a plurality of segments). The plurality of projection data respectively correspond to a plurality of cardiac cycles. Each of the plurality of projection data sets is a set of projection data acquired within a specific period having a predetermined time width which is centered on a specific cardiac phase (reconstruction central phase) designated by the examination plan setting unit 207.

If, for example, "desired specific cardiac phase: 65%", "segment reconstruction", and "segment count (projection data set count): 3", three projection data sets acquired within a predetermined period centered on a cardiac phase of 65% are selected from three continuous or discrete cardiac cycles. The three projection data sets covers 180°+fan angle.

Figure 4:
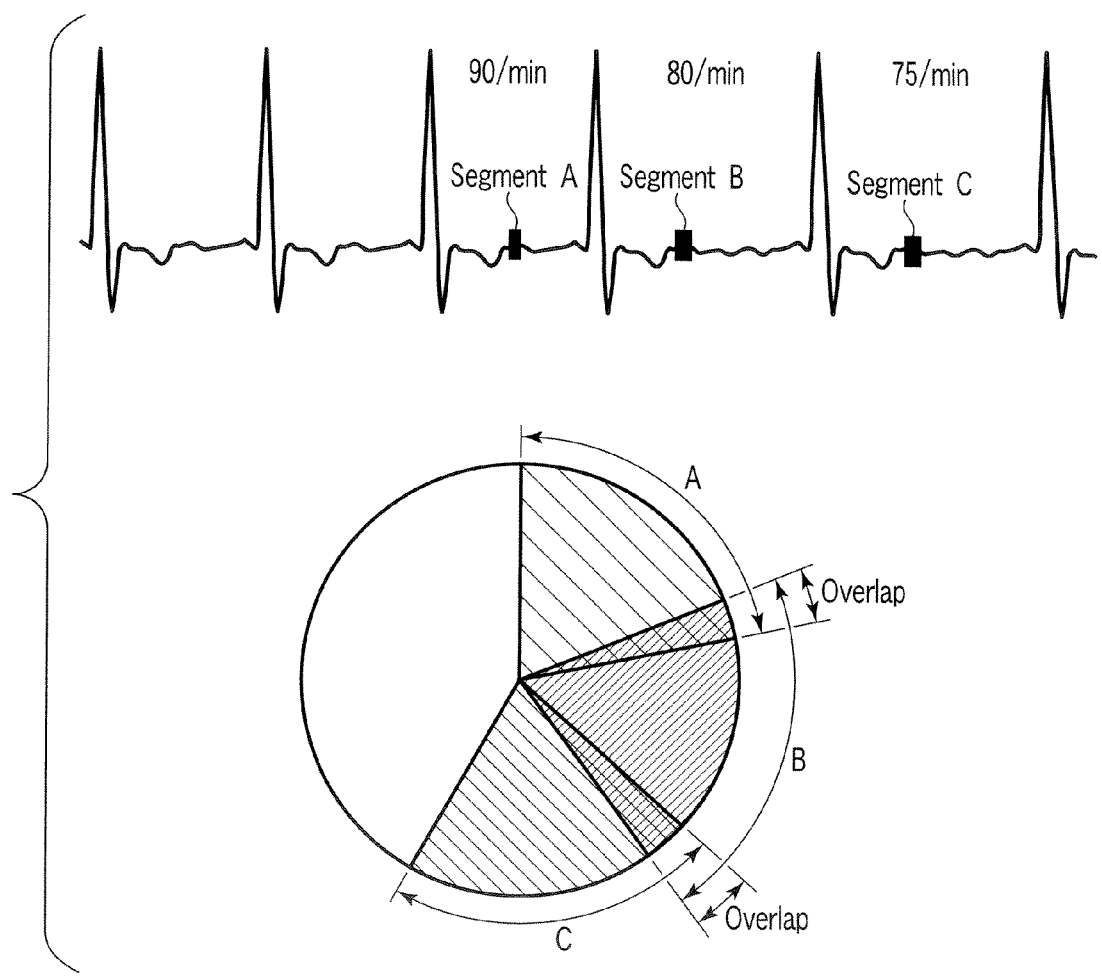
FIG. 4 is a diagram showing the overlaps between segments made by a reconstruction processing unit in FIG. 1.

As exemplified by FIG. 4, if three projection data sets (segments), A, B, and C partially overlap, i.e., projection data with the same view (the angle of the X-ray tube) exist between the plurality of segments, the image reconstruction processing unit 206 weights and adds the projection data of one segment and the projection data of the other segment for each view instead of selecting one of the projection data for each view. Weights are relatively determined in accordance with heart rates. As the heart rate decreases, a higher weight is attached, and vice versa. This makes it possible to reduce motion artifact. For example, weights are determined by the following equation. Letting HRA be a heart rate at the time of acquisition of the data of the segment A, and HRB be a heart rate at the time of acquisition of the data of the segment B which partially overlaps the segment A, WA as a weight for the projection data of the segment A can be given by $$WA = ((HRA + HRB) - HRA)/(HRA + HRB)$$
$$= HRB/(HRA + HRB)$$

A weight WB for the projection data of the segment B is given by $$WB = ((HRA + HRB) - HRB)/(HRA + HRB)$$
$$= HRA/(HRA + HRB)$$

When, for example, the heart rate at the time of acquisition of the segment A is 90 bps, and the heart rate at the time of acquisition of the segment B is 75 bps, the weight WA for the projection data of the segment A is 0.45, and the weight WB for the projection data of the segment B is 0.55.

A weight need not always correspond to a heart rate. For example, a weight is made to correspond to the occupation ratio of each projection data set to the angle range of (180+α) which is required for image reconstruction. A weight to be applied to projection data in a projection data set exhibiting a relatively high occupation ratio is set to be higher than that applied to projection data in a projection data set exhibiting a relatively low occupation ratio. If, for example, the heart rate at the time of acquisition of the segment A is 90 bps and the heart rate at the time of acquisition of the segment B is 75 bps, the weight WA for the projection data of the segment is set to 0.3, and the weight WB for the projection data of the segment is set to 0.7.

In this embodiment, the number of segments for segment reconstruction may be set by the examination plan setting unit 207. Assume, however, that the number of segments is automatically determined on the basis of the average heart rate acquired from the electrocardiograph 106 (or the storage unit 203) or the average heart rate and scanning speed (the rotational speed of the rotating frame 103) acquired from the system control unit 212.

The image reconstruction processing unit 206 reconstructs an image on the basis of the selected or collected projection data set. The image reconstruction processing unit 206 may comprise any one of a fan beam reconstruction processing function and a cone beam reconstruction processing function. In this embodiment, the image reconstruction processing unit 206 comprises both the fan beam reconstruction processing function and the cone beam reconstruction processing function, and reconstructs an image such as a tomogram by using at least one of the reconstruction processing functions set by the examination plan setting unit 207.

In this embodiment, when cone beam reconstruction processing is set by the examination plan setting unit 207, the image reconstruction processing unit 206 sequentially reconstructs tomograms by using fan beam reconstruction on the basis of the acquired projection data, in parallel with helical scanning, regardless of a cardiac phase designated and reconstructed by the examination plan setting unit 207 (the above case includes phases other than 65%, i.e., 0 to 100% projection data).

The image reconstruction processing unit 206 reconstructs a tomogram (or three-dimensional image) by cone beam reconstruction, after helical scanning or on the background, on the basis of the projection data which is selected for the reconstruction of a tomogram of a cardiac phase as the above reconstruction target. This allows the display unit 210 to display a tomogram almost in real time following helical scanning and display an accurate image based on the tomogram displayed in real time after helical scanning.

In this embodiment, as will be described later, the X-ray dose is changed (modulated) during scanning. It is, however, difficult for the operator to determine whether the X-ray dose has been changed during scanning. In this embodiment, since projection data is subjected to reconstruction processing by using fan beam reconstruction with a small calculation amount in parallel with scanning, a tomogram can be reconstructed almost in real time. The image SD of a tomogram changes as an X-ray dose is modulated. Since an operator is generally an X-ray engineer, he/she can recognize the modulation of an X-ray dose from a change in the image SD of a tomogram displayed in real time. Alternatively, displaying, on the display unit 210, a tomogram obtained by cone beam reconstruction, which is an accurate tomogram even though it requires a large calculation amount, after scanning makes it possible to perform diagnosis based on the tomogram more accurate than that obtained by the fan beam reconstruction method.

Target projection data to be subjected to fan beam reconstruction in parallel with scanning may be projection data acquired by all the detection element rows designated by the examination plan setting unit 207. In order to increase the calculation speed, however, target projection data is preferably projection data acquired by one detection element row of the X-ray detector 102 (e.g., the middle row in the slice direction, i.e., the 32nd or 33rd row in the middle of a 64-row detector) or the data obtained by adding projection data acquired by a plurality of rows of the X-ray detector 102 (e.g., a plurality of rows in the middle of a multi-row detector in the slice direction, i.e., the 31st, 32nd, 33rd, and 34th rows of the 64-row detector). Alternatively, real-time reconstruction in parallel with scanning may be implemented by reconstructing a tomogram by cone beam reconstruction processing on the basis of data acquired by some detection element rows (one or a plurality of rows) instead of using all the detection element rows in the data acquisition form set by the examination plan setting unit 207. An increase in calculation speed can also be achieved by cone beam reconstruction processing based on data acquired by some detection element rows in this manner.

As cone beam reconstruction processing, image reconstruction is preferably performed on the basis of projection data by using a reconstruction method called the Feldkamp method. The Feldkamp reconstruction method is an approximate reconstruction method which has been improved on the basis of the fan beam convolution back projection method and is used to generate three-dimensional distribution data of X-ray absorption coefficients (to be referred to as volume data (a stereoscopic (three-dimensional) set of a plurality of voxel data) by handling a target area wide in the slice direction (Z-axis direction) as an aggregate of a plurality of voxels). That is, in the Feldkamp reconstruction method, data is regarded as fan projection data and convoluted, and back projection is performed along an oblique ray corresponding to an actual cone angle with respect to the rotation center axis. Cone beam reconstruction processing may be performed such that projection data is three-dimensionally handled and subjected to cone-parallel conversion (rearranged into parallel beams), and three-dimensional back projection is performed on the basis of the rearranged projection data.

Fan beam reconstruction processing is performed by using, for example, the fan beam convolution back projection method, and image reconstruction is performed by back projection on the basis of projection data, assuming that an X-ray is perpendicular to the rotation axis of the X-ray tube 101 (the projection data has been obtained by an X-ray in a direction perpendicular to the Z-axis direction).

The reconstructed tomogram is temporarily stored in the image storage unit 209 and displayed on the display unit 210. Alternatively, the tomogram is converted into so-called pseudo three-dimensional image data such as a tomogram of an arbitrary slice, a projection image from an arbitrary direction, or a three-dimensional surface image of a specific organ which is obtained by rendering processing in accordance with an instruction from the operator. This data is then displayed on the display unit 210 through the image storage unit 209.

The examination plan setting unit 207 comprises a keyboard, various kinds of switches, a mouse, and the like and has a user interface function for allowing the operator to set an examination plan. The examination plan setting unit 207 includes a display unit (which is independent of or incorporated in the display unit 210) for supporting examination planning, and selects/generates an examination plan on a setting window displayed on the display unit 210. Parameters set for an examination plan include an examination target region, a sequence, scanning conditions for the acquisition of data of a subject (patient), reconstruction conditions for image reconstruction, display conditions for the display of a reconstructed image, the voice generation timing at the time of breathing exercise or during scanning, and the like.

Examination target regions as setting targets include a head portion, chest portion, abdominal portion, waist portion, lower limbs, and the like. Assume that in this embodiment, a plurality of examination target regions are displayed on a setting window of the examination plan setting unit 207, and the chest portion (the heart if it is included as a selection target) is selected.

Sequences that can be selected include a sequence from scanning to image reconstruction, a sequence from scanning to image transfer, sequence from scanning to image recording, and the like. In this embodiment, a sequence from scanning to image display is selected by the examination plan setting unit 207.

Scan conditions that can be set include a scan type, a data acquisition form indicating an acquisition form for scanning, a reconstruction range, conditions associated with ECG gated scanning, and the like. In this embodiment, as scanning types, the following three types are prepared: conventional scanning, helical scanning, and dynamic scanning. In this embodiment, a data acquisition form is represented by "slice count× slice thickness". Assume that as such forms, two types of conditions, i.e., "64×0.5" and "32×0.5", are stored in advance, and the examination plan setting unit 207 can select one of them. Assume that in this case, the examination plan setting unit 207 selects "64×0.5", i.e., the form of simultaneously acquiring data of 64 slices by 0.5 mm detection element rows. The data acquisition forms stored in advance are not limited to the above two types of forms, and three or more types of forms may be stored. Obviously, the above numerical values vary depending on the structure of the X-ray detector 102. A reconstruction range is also called a scanning period. Assume that in this embodiment, the start and end positions of such a range are input/set by the examination plan setting unit 207.

In this embodiment, the examination plan setting unit 207 sets, as conditions associated with ECG gated scanning, a cardiac phase to be reconstructed, a heart rate fluctuation range, an ECG gated reconstruction mode (either half reconstruction or segment reconstruction), a helical pitch, conditions associated with an X-ray dose in a standard scanning period, and the like. Note that no helical pitch is set when conventional scanning or dynamic scanning is selected. A heart rate may be a value per minute or an interval (R-R interval) from a given R wave to the next R wave.

A reconstruction cardiac is set in "%" or "msec". The unit "%" is based on the standardization of the interval from a given R wave to the next R wave with 0 to 100%, with 0% corresponding to the position of the R wave and 100% corresponding to the position of the next R wave, and expresses a position in the interval. The unit "msec" expresses a delay time (scanning delay time) with reference to the R wave. Assume that in this embodiment, the examination plan setting unit 207 sets the above data in %, the system control unit 212 automatically converts the data into a delay time before scanning, and the scanning control unit 201 performs control during scanning with reference to a delay time ms.

A cardiac phase to be reconstructed is, for example, a central phase which the operator wants to reconstruct, and is set as an arbitrary numerical value by using the keyboard or the like of the examination plan setting unit 207 or by displaying an electrocardiogram acquired before scanning on a display window and making a marking on the electrocardiogram. As a set cardiac phase, one of phases of 65 to 85% is preferably set to reduce motion artifact. Assume that in this embodiment, a phase of 75% is set as a cardiac phase to be reconstructed by using the examination plan setting unit 207.

A heart rate fluctuation range may be input in the form of numerical values such as 70 to 80 bpm by the operator using the examination plan setting unit 207, or may be set on a graph indicating the relationship between the time and heart rates as shown in FIG. 3A. When a heart rate fluctuation range is to be input in the form of numerical values, it is preferable to display a representative value of the heart rate of several heartbeats before scanning (e.g., a median value, average value, maximum heart rate, or minimum heart rate in a breathing exercise, i.e., a voice generation period or at the time of examination plan setting, or a combination thereof) as reference information on a display window. This allows the operator to efficiently set a heart rate fluctuation range. If such a range is to be set by using a graph showing the relationship between the time and heart rates, the range may be displayed parallel to an electrocardiogram as shown in FIG. 3A, or no electrocardiogram may be displayed.

Alternatively, a heart rate fluctuation range may be determined in advance as a default range like 80 to 100 bpm instead of being input or set by the operator in the above manner.

Figure 3B:
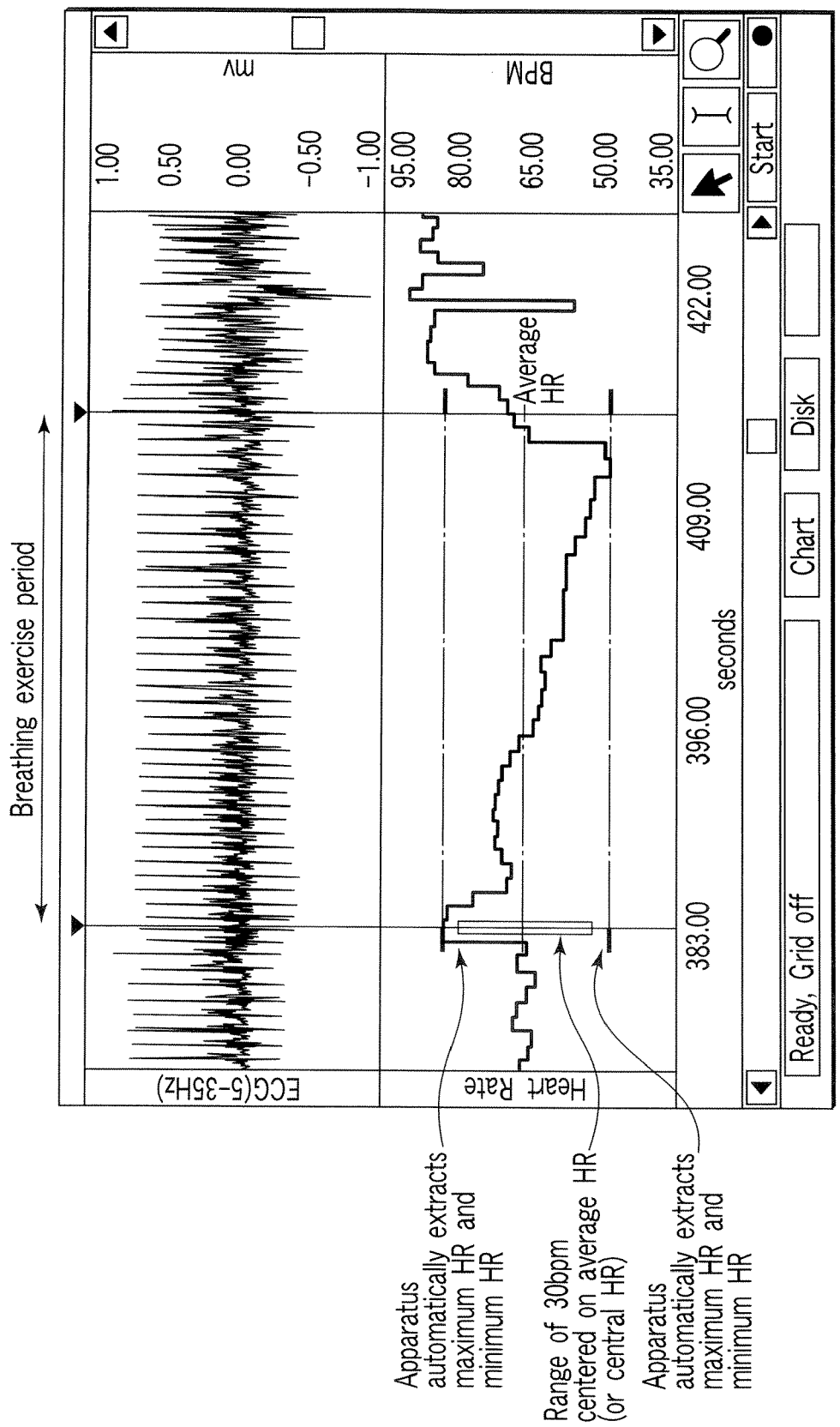
FIG. 3B is a diagram showing a heart rate fluctuation range automatically set by a system control unit in FIG. 1.

As shown in FIG. 3B, a heart rate fluctuation range may be automatically determined by the system control unit 212 on the basis of the above representative value of the heart rate of several heartbeats before scanning. For example, the breathing exercise period obtained by the system control unit 212 or the maximum and minimum heart rates at the time of examination plan setting may be determined as a heart rate fluctuation range, the maximum and minimum heart rates obtained upon omission of several higher and lower heart rates from heart rates obtained before scanning may be determined as a heart rate fluctuation range, or a range of 20 or 30 bpm centered on an average or median obtained before scanning may be determined as a heart rate fluctuation range.

Alternatively, a heart rate fluctuation range may be determined semi-automatically by making the display unit display, as a default range, a proper heart rate fluctuation range (e.g., maximum and minimum heart rates) of a set of heart rates obtained by the system control unit 212 before scanning, and allowing the operator to edit the displayed range by using a keyboard or the like.

Assume that in this embodiment, the operator inputs/sets a heart rate fluctuation range in the form of numerical values by using the examination plan setting unit 207. Before this setting, the examination plan setting unit 207 preferably activates a navigation window for setting conditions associated with ECG gated scanning on a display window, and displays at least an input box for a cardiac phase to be reconstructed, an input box for a condition associated with an X-ray dose, a selection box for an ECG gated reconstruction mode (half reconstruction/segment reconstruction), and the above representative value information display box, together with an input box for a heart rate fluctuation range. This allows the operator to identify and input conditions associated with ECG gated scanning and other conditions, and hence makes it possible to prevent operation errors.

The conditions associated with an X-ray dose in a standard scanning period include a tube current, a tube voltage, and the like, and the operator inputs numerical values such as a tube voltage of 135 kV and a tube current of 350 mA by using the examination plan setting unit 207. In general, a tube current is controlled by a filament current.

A standard scanning period is a period obtained by extending a segment period having a predetermined time width center on a specific cardiac phase with reference to a cardiac cycle used for setting the specific cardiac phase on the basis of the heart rate fluctuation range of a subject. Alternatively, a standard scanning period is a period obtained by extending a segment period set with reference to an average cardiac cycle associated with the subject on the basis of the heart rate fluctuation range of the subject. Note that a segment period is defined as a period during which a projection data set required for the reconstruction of a tomogram is acquired.

More specifically, the start point of a standard scanning period is made to coincide with the start point of a segment period corresponding to the maximum heart rate (the shortest cardiac cycle), and the end point of the standard scanning period is made to coincide with the end point of a segment period corresponding to the minimum heart rate (the longest cardiac cycle).

A high dose of X-rays is maintained throughout this standard scanning period. This makes it possible to permit even fluctuations in the heart rate of the subject. A projection data set with a high SNR can be extracted from any time point in the standard scanning period. A tomogram with high image quality can be generated from the projection data set with high SNR.

For the sake of descriptive convenience, the expression "standard scanning period" is used. However, this period may be expressed as a first period or the like. Note that a period in a cardiac period except for a standard scanning period will be referred to as a low dose scanning period (or a second period). In the second period, a generation of X-rays may be stopped.

In addition, the examination plan setting unit 207 may be used to input tube voltages and tube currents in both a standard scanning period and a low X-ray dose scanning period (in this case, control is preferably performed to inhibit a tube current value in a low X-ray dose scanning period from being set to be larger than that in a standard X-ray scanning period). In this embodiment, a tube voltage and tube current in a standard scanning period are set. This makes it possible to prevent the operator from performing erroneous operation and reduce the load imposed on the operator.

The examination plan setting unit 207 inputs a reconstruction scheme (fan beam reconstruction/cone beam reconstruction), reconstruction slice thickness, reconstruction interval, and the like as reconstruction conditions. Assume that in this embodiment, cone beam reconstruction is set as a reconstruction scheme.

The examination plan setting unit 207 also sets a window level, a window width, and the like as image display conditions.

The examination plan set by the examination plan setting unit 207 is transmitted to the system control unit 212. The system control unit 212 has a program for causing the examination plan setting unit 207 to put a set examination plan into practice, and controls the scanning control unit 201, projection data storage unit 203, image reconstruction processing unit 206, and the like. This systematic control by the system control unit 212 implements a sequence from scanning to image reconstruction.

The system control unit 212 reads out the electrocardiographic data (electrocardiographic signal) acquired by the electrocardiograph 106 from the projection data storage unit 203 in synchronism with scanning, and extracts, for example, an R wave from the electrocardiographic data. The system control unit 212 also reads out the electrocardiographic data acquired by the electrocardiograph 106 from the projection data storage unit 203, and obtains the heart rate of a plurality of heartbeats. The system control unit 212 further acquires the above representative value (the average of heart rates, the maximum heart rate, the minimum heart rate, or the like) from the heart rate of a plurality of heartbeats.

The system control unit 212 determines, on the basis of the cardiac phase to be reconstructed and the heart rate range (heart rate fluctuation range) set by the examination plan setting unit 207, a standard X-ray dose scanning period (the period of a tube current value set when a cardiac phase to be reconstructed and a margin/error range are scanned) during which scanning is performed by using the tube current value set by the examination plan setting unit 207 and a low X-ray dose scanning period (the period of a tube current value smaller than the tube current value in the standard X-ray dose scanning period) during which scanning is performed by using a tube current value smaller than that in the scanning period. A standard X-ray dose scanning period and low X-ray dose scanning period are preferably calculated in terms of delay times from an R wave. The system control unit 212 may be configured to calculate a standard X-ray dose scanning period and a low X-ray dose scanning period on the basis of the cardiac phase to be reconstructed and the heart rate fluctuation range which are set by the examination plan setting unit 207. However, the examination plan setting unit 207 is preferably configured to have a storage unit in which standard X-ray dose scanning periods and low X-ray dose scanning periods are stored in association with cardiac phases to be reconstructed and heart rate ranges and to determine a standard X-ray dose scanning period and a low X-ray dose scanning period in accordance with the cardiac phase to be reconstructed and the heart rate fluctuation range which are set by the examination plan setting unit 207.

A method of determining a standard X-ray dose scanning period (the period of a set tube current value) and a low X-ray dose scanning period (the period of a low tube current value for modulation) will be described in detail below with reference to FIGS. 2A to 2E.

FIG. 2A shows a change in heart rate before scanning, e.g., at the time of breathing exercise. FIG. 2B shows a change in heart rate when a subject is actually scanned. FIG. 2C shows an electrocardiogram of a maximum heart rate, which is obtained before scanning, with reference to an R wave acquired at the time of actual scanning. FIG. 2D shows an electrocardiogram of a minimum heart rate, which is obtained before scanning, with reference to the R wave acquired at the time of actual scanning. Note that each open rectangular mark in FIGS. 2A to 2E indicates a cardiac phase to be reconstructed.

As shown in FIG. 2B, assume that the heart rate at the time of scanning has changed from 60 bpm to 60 bpm, 83 bpm, 83 bpm, and 83 bpm. When the operator sets 75% from an R wave as a phase in which the operator wants to reconstruct an image, X-rays are applied to only an open rectangular mark at a standard X-ray dose (an X-ray dose with 300 mA in FIG. 2E). It is ideal that during other periods, no X-rays are applied. However, it is not accurately known before scanning how the heart rate will change at the time of scanning.

According to this method, the error range of heart rates during a scanning period is predicted from heart rates corresponding to a plurality of periods which are acquired before scanning. In this case, since the heart rate at the time of breathing exercise changes from 60 bpm to 60 bpm, 83 bpm, 83 bpm, and 90 bpm as shown in FIG. 2A, fluctuations in heart rate at the time of scanning can be predicted such that the maximum heart rate becomes 90 bpm, and the minimum heart rate becomes 60 bpm. In a breathing exercise, in particular, since the subject stops breathing as in the case of scanning, it is effective to predict a heart rate fluctuation range, i.e., a maximum heart rate and a minimum heart rate, at the time of scanning by using heart rates corresponding to a plurality of period during the breathing exercise.

An R wave is picked up from electrocardiographic information synchronously acquired during scanning. With reference to this R wave, a reconstruction cardiac phase of 75% of a maximum heart rate of 90 bpm is determined as the start position of a standard scanning period, a reconstruction cardiac phase of 75% of a minimum heart rate of 60 bpm is determined as the end position of the standard scanning period, and the remaining cardiac phase is determined as a low X-ray dose scanning period. These start and end positions are converted into delay times from the R wave. As an X-ray dose in a standard scanning period (conditions associated with an X-ray dose which include at least a tube current value of a tube current value and a tube voltage value), the tube current value set by the examination plan setting unit 207 is used. An X-ray dose or conditions associated with an X-ray dose in a low X-ray dose scanning period may be automatically determined in accordance with the set conditions for the standard scanning period. More specifically, as an X-ray dose or conditions associated with an X-ray dose in the low X-ray dose scanning period, an X-ray dose or conditions associated with an X-ray dose which are about ⅓ to ½ that or those in the standard scanning period (if, for example, the set tube current value and set tube voltage value in the standard scanning period are 300 mA and 135 kV, respectively, a tube current value in the low X-ray scanning period is ⅓ of the set tube current value, i.e., 100 mA, and a tube voltage value is equal to the set tube voltage value, i.e., 135 kV) are determined in advance. Alternatively, conditions associated with an X-ray dose in the low X-ray dose scanning period are determined to be fixed values (e.g., the tube current value and tube voltage value are determined to be 90 mA an 125 kV, respectively).

The period setting method using a maximum heart rate and a minimum heart rate has been described with reference to FIGS. 2A to 2E. Obviously, however, a heart rate fluctuation range may be set by using various kinds of values, e.g., the maximum and minimum heart rates obtained upon omission of several higher and lower heart rates from all the heart rates obtained before scanning, and a predetermined range (for example, 60 to 80 bpm, which are respectively higher and lower than an average of 70 bpm by 10 bmp) from an average or median obtained before scanning.

This embodiment has exemplified the case wherein a heart rate fluctuation range can be arbitrarily set by the examination plan setting unit 207. If, however, the range of numerical values input by the operator or the range of a line cursor exceeds a threshold, it is preferable to inhibit the range from being confirmed (inhibit an examination plan from being confirmed) so as to prevent the use of this modulation. This is because since the heart rate fluctuation range of an actual patient hardly exceeds 15 to 30 bpm at the time of scanning, and a patient who exhibits a large heart rate fluctuation range is predicted to have arrhythmia, it is not preferable to use such values without any change.

The system control unit 212 supplies an X-ray control signal for controlling the modulation of an X-ray dose to the scanning control unit 201 in accordance with the standard scanning period determined in the above manner or a standard scanning period and a low X-ray dose scanning period. If, for example, the X-ray control signal is at LOW level, a tube voltage and tube current for a low dose are applied from the high voltage generator 104 to the X-ray tube 101 to generate a low dose of X-rays from the X-ray tube 101. If the X-ray control signal is at HIGH level, since a tube voltage and tube current for a high dose (the tube voltage value and tube current value set by the examination plan setting unit 207 in this case) are applied from the high voltage generator 104 to the X-ray tube 101, the X-ray tube 101 generates a high dose of X-rays. The system control unit 212 sets the X-ray control signal at LOW level in a low X-ray dose scanning period, and sets the X-ray control signal at HIGH level in a standard scanning period. With this operation, X-rays are applied at a low dose in the low X-ray dose scanning period, and are applied at a high dose in the standard scanning period. Even if, therefore, the heart rate of the subject fluctuates during scanning, projection data required to reconstruct a desired cardiac phase can be reliably obtained, and a reduction in exposure during a period irrelevant to diagnosis can be achieved.

Although the system control unit 212 performs control to scan at a high X-ray dose in a standard scanning period and at a low X-ray dose in a low X-ray dose scanning period, the tube current or the like (or the X-ray dose) to be supplied from the high voltage generator 104 to the X-ray tube 101 is not abruptly switched from a low X-ray dose scanning period to a standard scanning period. That is, as shown in FIG. 2E, the system control unit 212 gradually changes a tube current or the like (or an X-ray dose) from the high voltage generator 104 in a transition period between a low X-ray dose scanning period and a standard scanning period. The system control unit 212 controls a tube current in a low X-ray dose scanning period so as to prevent the current from becoming equal to or less than a predetermined threshold (tube current value) except when the examination plan setting unit 207 sets otherwise. Such control is performed to prevent failures caused by overloads on the X-ray tube 101 and high voltage generator 104 when a tube current is abruptly increased from a low X-ray dose scanning period to a standard scanning period or abruptly decreased from a standard scanning period to a low X-ray dose scanning period.

The system control unit 212 supplies control signals to the scanning control unit 201 to systematically perform rotation control on the rotating frame 103 and movement control on the top 302 in addition to X-ray adjustment control on the scanning control unit 201. Upon receiving these control signals, the scanning control unit 201 performs various types of control and acquires projection data in accordance with the signals. The projection data is temporarily stored in the projection data storage unit 203 in association with a view, the channel number and row number of the X-ray detector 102, and an electrocardiographic signal (electrocardiographic data). The image reconstruction processing unit 206 sequentially reconstructs tomogram data from the projection data stored in the projection data storage unit 203 by using the fan beam reconstruction method in parallel with scanning, and reconstructs tomogram data in all scanning periods by using the cone beam reconstruction method after the scanning (or on the background). The tomogram data reconstructed by the image reconstruction processing unit 206 is supplied to the display unit 210 through the image storage unit 209 and displayed on the display unit 210.

The operation of the X-ray computed tomography apparatus having the above arrangement will be described next.

Cardiac examination using the X-ray computed tomography apparatus according to this embodiment is roughly performed in the following procedure: breathing exercise, examination plan setting, scanning, image reconstruction, and other processing.

First of all, the operator makes the subject perform breathing exercise before scanning. In breathing exercise, the operator attaches an electrode to the subject, and checks whether electrocardiographic signals are accurately acquired by the electrocardiograph 106. Upon confirming that the electrocardiograph 106 can acquire electrocardiographic signals, the operator makes the subject perform breathing exercise in accordance with a breathing exercise function provided for this apparatus. The operator sets a breath holding period by using the examination plan setting unit 207. Subsequently, when the operator issues an instruction to start by using the examination plan setting unit 207, a voice guidance like "take in breath", "hold the breath", or "stop it" is generated from the gantry device 1. The electrocardiograph 106 acquires electrocardiographic information in a voice generation period, i.e., a breathing exercise period, and transmits the information to the console 2. The console 2 transmits the received electrocardiographic information to the system control unit 212 through the storage unit 203. The system control unit 212 obtains a heart rate for each period (R wave-R wave interval) in a breathing exercise period.

The operator makes an examination plan for cardiac examination by using the examination plan supporting function provided for this apparatus. More specifically, the operator selects the chest portion (the heart if it is included as a selection target) as an examination target region by using the examination plan setting unit 207. If the heart is selected as an examination target region, detailed parameter support information for the heart is displayed on a setting window on the examination plan setting unit 207. The operator inputs scanning conditions, reconstruction conditions, and the like by using the keyboard, mouse, and the like of the examination plan setting unit 207 while referring to this support information. The scan conditions to be input and set include a scanning type (helical scanning in this case), a data acquisition form (simultaneously acquiring 64 slices with 0.5 mm detection element rows/simultaneously acquiring 32 slices with 1.0 mm detection element rows), the start and end positions of a reconstruction range, conditions associated with ECG gated scanning, and the like. The reconstruction conditions to be input include a reconstruction scheme (fan beam reconstruction method/cone beam reconstruction method), a reconstruction slice count, a reconstruction slice thickness, and the like. In this embodiment, as a reconstruction scheme, the cone beam reconstruction method is selected.

The conditions associated with ECG gated scanning which are set include a cardiac phase to be reconstructed, a heart rate fluctuation range, a reconstruction mode (half reconstruction/segment reconstruction), a helical pitch, a scanning speed, and conditions (a tube current and a tube voltage) associated with an X-ray dose in a standard scanning range.

When the operator selects such an examination plan and clicks the confirmation button, information associated with the selected examination plan is transferred to the system control unit 212.

The system control unit 212 determines a standard X-ray dose scanning period and a low X-ray dose scanning period in accordance with the cardiac phase to be reconstructed and the heart rate fluctuation range which are set by the examination plan setting unit 207. The system control unit 212 obtains a standard X-ray dose scanning period and low X-ray dose scanning period as delay times from an R wave.

Upon confirming that the electrocardiograph 106 acquires an electrocardiographic signal, the operator issues an instruction to start examination by using the examination plan setting unit 207. Upon receiving this start instruction signal, the system control unit 212 controls the scanning control unit 201, projection data storage unit 203, image reconstruction processing unit 206, and the like.

The scanning control unit 201 controls the gantry driving device 105 and the bed driving device 301 to make the gantry driving device 105 rotate the rotating frame 103 so as to reach the scanning speed set by the examination plan setting unit 207, and to make the bed driving device 301 move the top 302 to a position immediately before a scanning start position (an approach position for helical scanning).

When the speed of the rotating frame 103 reaches the set speed, the bed driving device 301 slides the top 302 in the slice direction (Z-axis direction). When the slide speed of the top 302 becomes constant, the high voltage generator 104 supplies the tube voltage and tube current set by the examination plan setting unit 207 to the X-ray tube 101 to apply X-rays.

When the high voltage generator 104 supplies the tube voltage and the tube current to the X-ray tube 101, the system control unit 212 performs the following processing.

The system control unit 212 reads out the electrocardiographic data (electrocardiographic signal) acquired by the electrocardiograph 106 in synchronism with scanning from the storage unit 203, and sequentially picks up R waves from the electrocardiographic data (electrocardiographic signal). The system control unit 212 transmits an X-ray control signal for X-ray dose modulation control to the scanning control unit 201 on the basis of an R wave of the synchronously acquired electrocardiographic signal and delay times from the R wave in the determined standard scanning period and low X-ray dose scanning period. The scanning control unit 201 transmits an X-ray control signal indicating HIGH level so as to apply a high dose of X-rays with a delay time from the R wave in the standard scanning period, and transmits an X-ray control signal indicating LOW level so as to apply a low dose of X-rays with a delay time from the R wave in the low X-ray dose scanning period.

The high voltage generator 104 receives an X-ray control signal from the scanning control unit 201, and supplies the tube voltage and tube current set by the examination plan setting unit 207 to the X-ray tube 101 if the signal is at HIGH level. If the X-ray control signal from the scanning control unit 201 is at LOW level, the high voltage generator 104 sets the same tube voltage as that set at HIGH level, and supplies a tube current about ⅓ the tube current value at HIGH level. With this operation, X-rays are applied at a high dose from the X-ray tube 101 in the standard scanning period, and X-rays are applied at a low dose in the low X-ray dose scanning period. When a transition is made from a standard scanning period to a low X-ray dose scanning period, a tube current (X-ray dose) gradually decreases in the transition period and becomes a tube current value (X-ray dose) ⅓ that in the low X-ray dose period. When a transition is made from a low X-ray dose scanning period to a standard scanning period, the tube current (X-ray dose) gradually decreases in the transition period, and becomes the tube current value (X-ray dose) set in the standard scanning period.

In this manner, the electrocardiograph 106 acquires an electrocardiographic signal in parallel with helical scanning in the data acquisition form set by the examination plan setting unit 207, thereby modulating the X-ray dose during helical scanning.

The X-rays transmitted through the subject are detected by the rotating frame 103 and converted into the projection data of an analog electrical signal. The data acquisition device 107 converts this data into the projection data of a digital electrical signal. The data is then sent to the pre-processing unit 202 through a data transmission unit (not shown) to be subjected to various kinds of correction processing.

The projection data storage unit 203 of the console 2 stores projection data together with electrocardiographic data (electrocardiographic signal) from the electrocardiograph 106, in association with a view representing the rotation angle of the X-ray tube 101 at the time of data acquisition, a channel number, a row umber, and the like.

The image reconstruction processing unit 206 performs real-time reconstruction, in parallel with helical scanning, on the basis of the projection data acquired by some detection element rows, of the data acquisition form (all detection element rows), which are set by the examination plan setting unit 207, to sequentially reconstruct tomograms, and the display unit 210 displays the sequentially reconstructed tomograms. The image reconstruction processing unit 206 weights data associated with a cardiac phase to be reconstructed which is designated by the examination plan setting unit 207 (in this case, projection data of the same cardiac phase which are acquired by segment reconstruction) after helical scanning or on the background, and reconstructs a plurality of tomograms in the reconstruction range set by the examination plan setting unit 207 by using cone beam reconstruction with a set image pitch and a set image slice thickness. The display unit 210 then displays a tomogram obtained by cone beam reconstruction.

As described above, in this embodiment, when an X-ray dose is to be demodulated in ECG gated scanning, scanning is performed under set X-ray conditions in a margin period as well as in a period required for the reconstruction of a designated cardiac phase to be reconstructed. This makes it possible to obtain the projection data of the cardiac phase to be reconstructed at the X-ray dose designated by the operator (i.e., an image with a desired S/N) while reducing the exposure to the subject even if the heart rate (R-R interval) of the subject fluctuates.

In this embodiment, scanning can be performed upon prediction of fluctuations in heart rate at the time of scanning, i.e., an error range, by determining a standard scanning period on the basis of a plurality of heart rates acquired before scanning and the cardiac phase to be reconstructed which is designated by the operator. This makes it possible to reliably obtain the data of the cardiac phase to be reconstructed which is desired by the operator while a reduction in exposure to the subject is achieved.

In addition, in this embodiment, a standard scanning period is determined on the basis of a plurality of heart rates in a breathing exercise period. Since the subject holds his/her breath in a breathing exercise period at the time of scanning, a heart rate fluctuation range can be accurately predicted.

In this embodiment, maximum and minimum heart rates are picked up from a plurality of heart rates acquired before scanning and are used as a heart rate fluctuation range, thereby increasing the prediction accuracy of the heart rate fluctuation range at the time of scanning.

In this embodiment, since it suffices to make the operator set only X-ray conditions (a tube voltage and a tube current) in a standard scanning period of the standard scanning period and a low dose scanning period, it can prevent an error of setting X-ray conditions for a low X-ray dose in a standard scanning period and X-ray conditions for a high X-ray dose in a low dose scanning period.

In this embodiment, real-time reconstruction is performed, in parallel with helical scanning, on the basis of the projection data acquired by some detection element rows, of all the detection element rows of the data acquisition form, which are set by the examination plan setting unit 207, to sequentially reconstruct tomograms, and the display unit 210 displays the sequentially reconstructed tomograms. A tomogram is reconstructed by using cone beam reconstruction after the end of helical scanning or on the background on the basis of projection data associated with the cardiac phase to be reconstructed which is designated by the examination plan setting unit 207. This allows the operator to check a tomogram in real time, and hence the operator can check on the basis of a change in image SD whether the X-ray dose is modulated. In addition, after the scanning, diagnosis can be performed with an accurate tomogram.

In addition, in this embodiment, providing a transition period between a standard scanning period and a low X-ray dose scanning period and providing a limitation to inhibit a tube current in a low X-ray dose scanning period from becoming equal to or less than a given value makes it possible to prevent an excessive load from being imposed on the X-ray tube 101 and the like and prevent failures.

Note that the present invention is not limited to the above embodiment, and constituent elements can be variously modified and embodied at the execution stage within the spirit and scope of the invention. Various inventions can be formed by proper combinations of a plurality of constituent elements disclosed in the above embodiments. For example, several constituent elements may be omitted from the all the constituent elements in the embodiment.

In this embodiment, for example, scanning is performed at the X-ray dose based on the set X-ray conditions in a standard scanning period, and scanning is performed at a lower X-ray dose in a low X-ray dose scanning period than in the standard scanning period (set X-ray conditions). However, X-rays applied to a subject in a low X-ray dose scanning period may be stopped/shielded, or the low X-ray dose scanning period may be provided with a period in which the X-ray dose is 0.

According to the above description of the embodiment, a heart rate fluctuation range is set by the examination plan setting unit 207 and is determined by the system control unit 212. However, it is not always necessary to set/determine a heart rate fluctuation range. Instead of this operation, it suffices to input/set a margin phase as well as a central phase when a cardiac phase to be reconstructed is set by the examination plan setting unit 207, or a margin phase may be determined on the basis of the cardiac phase to be reconstructed. This makes it possible to perform scanning at a high X-ray dose to a slightly excessive extent for data required for a reconstruction central phase in at least one heart rate. Even if, therefore, slight heart rate fluctuations occur during scanning, an image of a desired reconstruction central phase can be reconstructed while a reduction in exposure is achieved, thereby saving the labor of inputting/setting a heart rate fluctuation range.

Furthermore, it suffices to determine a heart rate fluctuation range (or more directly, a standard scanning period) on the basis of the heart rate of one or more heartbeats acquired during scanning instead of setting a heart rate fluctuation range from electrocardiographic information before scanning, for example, at the time of breathing exercise.

Alternatively, a heart rate fluctuation range may be determined in accordance with pieces of electrocardiographic information both before scanning and during scanning. If the heart rate obtained in accordance with electrocardiographic information acquired in parallel with scanning exceeds the heart rate fluctuation range determined before scanning, the X-ray dose based on the set tube current and tube voltage is maintained without X-ray modulation even during scanning.

This makes it possible to obtain the data of a cardiac phase to be reconstructed even if arrhythmia or the like occurs in the patient during scanning.

In addition, it suffices to make the system control unit 212 calculate a heart rate corresponding to a plurality of periods on the basis of electrocardiographic data stored in the projection data storage unit 203 which is acquired before scanning and automatically set a heart rate fluctuation range instead of making the operator input a heart rate fluctuation range. In this case, a heart rate as a reference with which a heart rate fluctuation range is automatically set may be an average value or median value instead of a maximum heart rate or a minimum heart rate.

In addition, it suffices to perform scanning with a set tube current value in a period obtained by adding a slight margin (e.g., several % or several msec) to a standard scanning period without setting a period which one-to-one corresponds to a cardiac phase to be reconstructed in a heart rate fluctuation range (e.g., a maximum heart rate and a minimum heart rate).

Only information associated with some heart rates (which correspond to e.g., several heartbeats from the start of breath holding and several heartbeats immediately before the end of breath holding) in a breath holding exercise period or only the electrocardiogram of some cardiac phases is displayed on the display unit of the examination plan setting unit 207. The operator may be allowed to set a heart rate and a cardiac phase to be reconstructed while referring to this display. As shown in FIGS. 3A and 3B, the heart rate tends to become maximum immediately after breath holding, then gradually decrease, and become minimum near the end of breath holding. For this reason, according to the arrangement of this modification, since the operator sets a cardiac phase to be reconstructed by using an electrocardiogram corresponding to the maximum and minimum heart rates, consideration may be given to an error lower than the maximum heart rate and an error higher than the minimum heart rate. In this case, the system control unit 212 determines a standard scanning period as follows. The system control unit 212 calculates the heart rate or electrocardiogram designated by the operator as the maximum heart rate and a heart rate lower than the maximum heart rate by 10 to 20 bpm as the minimum heart rate, and determines the time corresponding to the maximum heart rate as the start time of the standard scanning period and the time corresponding to the minimum heart rate as the end time of the standard scanning period. When the heart rate or electrocardiogram of several heartbeats immediately before the end of breath holding is displayed, the operator calculates the heart rate or electrocardiogram designated by the operator as the minimum heart rate and a heart rate higher than the minimum heart rate by 10 to 20 bpm as the maximum heart rate, and determines the time corresponding to the minimum heart rate as the end time of the standard scanning period and the time corresponding to the calculated maximum heart rate as the start time of the standard scanning period.

Although this embodiment has exemplified the case wherein the X-ray dose (or tube current value) in a standard scanning period is constant, the X-ray dose in the standard scanning period may be changed in a plurality of steps. For example, slightly high X-ray doses (tube current values) are set for predetermined views (e.g., 45°-135° and 225°-270°) in a standard scanning period, and slightly low X-ray does are set for other views (e.g., 315°-45° and 135°-225°), thus setting tube current values at a plurality of levels in a standard scanning period on the basis of projection data acquired by scout scanning for a scout image for reconstruction range positioning.

In this embodiment, a tube current value in a low X-ray dose scanning period is determined on the basis of a set tube current value in a standard scanning period or is set by the examination plan setting unit 207. However, the present invention is not limited to this. Assume that pre-scanning is to be performed to obtain a contrast medium injection timing before scanning of the heart, that is, a tomogram is reconstructed in real time on the basis of projection data obtained by monitoring scanning on the upstream side of the heart (e.g., the cervical region) for which a dose lower than that for scanning of the heart is set, and a value increasing from a CT value or mask image is to be displayed on the display unit 210. In this case, it may be determined that the tube current value in the low X-ray dose scanning period changes between a set tube current value in the standard scanning period as an upper limit and a tube current value in the low X-ray dose scanning period as a lower limit. This makes it unnecessary for the operator to determine three kinds of tube current values in a standard scanning period, monitoring scanning period, and low X-ray dose scanning period, thereby reducing the labor of the user in setting X-ray conditions.

In addition, in this embodiment, segment reconstruction is performed by acquiring segments (patches) corresponding to two or more heartbeats. However, there is the possibility of acquiring unnecessary patches due to the relationship between heart rates, rotational speeds, and the like. When, for example, projection data corresponding to half scanning (180°+fan angle) can be acquired in three segments at the first heartbeat, the second heartbeat, and the fourth heartbeat, the third heartbeat overlaps part of the first heartbeat and part of the second heartbeat. However, X-rays are applied in a cardiac phase at the third heartbeat to acquire the projection data of the segment corresponding to the fourth heartbeat. In such a case, the system control unit 212 performs control to perform scanning with the tube current value in a standard scanning period with respect to the three segments (cardiac phases) corresponding to the first, second, and fourth heartbeats and perform scanning with a tube current value for low dose scanning with respect to the segment (cardiac phase) corresponding to the third heartbeat. That is, when the overlapping portions between segments in segment reconstruction are large, the system control unit 212 determines a low X-ray dose scanning period for at least one segment (cardiac phase) instead of a standard scanning period. In other words, when the data of the same view (patch) is to be acquired a plurality of number of times, at least one of the plurality of times of acquisition is determined as a low X-ray dose scanning period instead of a standard scanning period. This makes it possible to further reduce exposure of the subject.

Second Embodiment

The second embodiment of an X-ray computed tomography apparatus (also called as an X-ray CT or CT scanner) according to the present invention will be described below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements are arrayed in the form of a ring, and only an X-ray tube rotates around a subject to be examined. The present invention can be applied to either type. In this case, the rotate/rotate type, which is currently the mainstream, will be exemplified.

In addition, reconstruction methods include the full reconstruction method, half reconstruction method, and segment reconstruction method. These reconstruction methods differ in angle range required to reconstruct one-slice tomogram data. Note that the time required for the X-ray tube to rotate throughout the angle range required for the reconstruction of one-slice tomogram data is called time resolution. In the full reconstruction method, projection data acquired while the X-ray tube rotates through 360° is required to reconstruct one-slice tomogram data. In the half reconstruction method, projection data acquired while the X-ray tube rotates through (180°+α) is required to reconstruct one-slice tomogram data. Note that α represents the spreading angle of X-rays, i.e., a fan angle. The segment reconstruction method is a method of preparing (180°+α) projection data by acquiring projection data in the range of {(180/n)°+α/n}, where n is the number of segments, from continuous or discrete n cardiac cycles. Time resolution in this segment reconstruction method is given as the time required for the X-ray tube to rotate throughout the angle range of {(180/n)°+α/n}. The present invention can be applied to either reconstruction scheme. In this case, the half scanning method will be exemplified.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. An X-ray detection element can employ either of these schemes. In this case, the former type, i.e., the indirect conversion type, will be exemplified. Recently, with advances toward the commercialization of a so-called multi-tube type X-ray computed tomography apparatus having a plurality of pairs of X-ray tubes and X-ray detectors mounted on a rotating ring, related techniques have been developed. The present invention can be applied to both a conventional single-tube type X-ray computed tomography apparatus and a multi-tube type X-ray computed tomography apparatus. The single-tube type X-ray computed tomography apparatus will be exemplified here.

FIG. 5 shows the arrangement of an X-ray computed tomography apparatus according to this embodiment. This X-ray computed tomography apparatus includes a gantry 1 configured to acquire projection data associated with a subject to be examined. The gantry 1 includes an X-ray tube 10 and a multi-channel X-ray detector 23. The X-ray tube 10 and the multi-channel X-ray detector 23 are mounted on an annular rotating frame 12 rotated/driven by a gantry driving device 25 so as to face each other through an opening portion in a central portion. When scanning is to be performed, a subject P placed on a top 2a of a bed 2 is inserted into the opening portion. An electrocardiograph 22 is attached to the subject P to detect an electrocardiogram of the subject P.

The multi-channel X-ray detector 23 is placed adjacent to a reference X-ray detector 24. X-rays which are not transmitted through the subject are applied to the reference X-ray detector 24. The reference X-ray detector 24 detects the output intensity of X-rays which have been generated from the X-ray tube 10 and have been hardly attenuated, and generates the resultant data (to be referred to as X-ray output data). The reference X-ray detector 24 can be replaced by another constituent element which can generate X-ray output data representing the output intensity of X-rays, e.g., an ammeter (11-1 in FIG. 6) which measures the tube current of the X-ray tube 10 or an ammeter (11-2 in FIG. 6) which measures the filament current of the X-ray tube 10.

Figure 6:
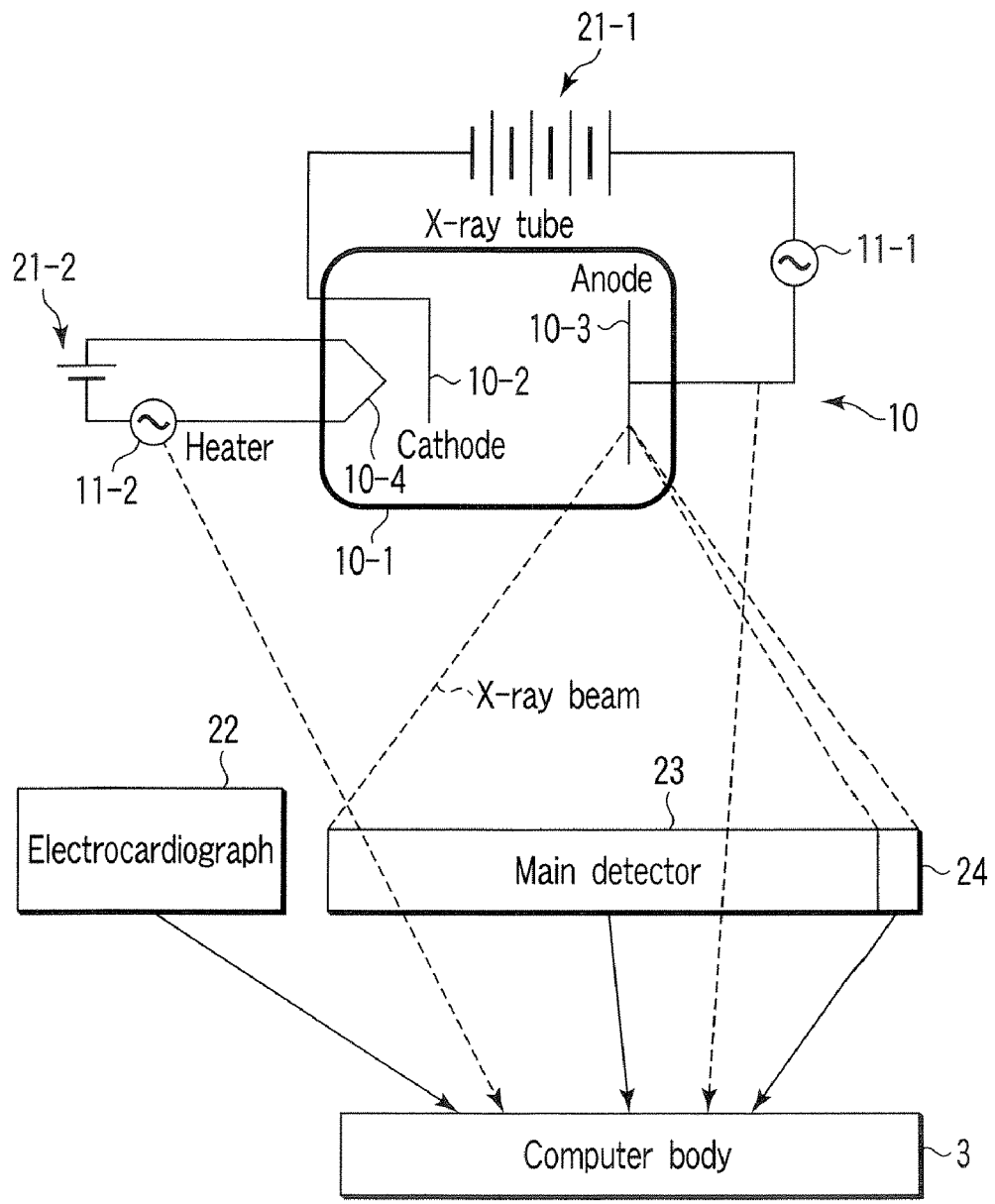
FIG. 6 is a schematic view of an X-ray tube in FIG. 1.

As shown in FIG. 6, a tube voltage generating unit 21-1 of a high voltage generator 21 applies a high voltage (tube voltage) between a cathode 10-3 and an anode 10-2 which are placed in a vacuum in a glass tube 10-1. A filament current is supplied from a filament current generating unit 21-2 of the high voltage generator 21 to a filament 10-4 of the X-ray tube 10. The thermoelectrons generated upon supply of the filament current are accelerated under high voltage and collide with the tungsten target of the anode 10-2, thereby generating X-rays.

Referring back to FIG. 5, a data acquisition device 26 generally called a DAS (Data Acquisition System) converts a signal output from the X-ray detector 23 for each channel into a voltage signal, amplifies it, and further converts it into a digital signal. This data (also called raw data) is supplied to a computer unit 3 placed outside the gantry.

A pre-processing unit 34 of the computer unit 3 performs correction processing such as sensitivity correction for the data (raw data) output from a data acquisition unit 26. This projection data is sent to a projection data storage device 37 of the computer unit 3 and is stored together with a time code. Electrocardiographic data from the electrocardiograph 22 is also stored in the projection data storage device 37.

In addition to the pre-processing unit 34 and the projection data storage device 37, the computer unit 3 comprises a system controller 29, input device 39, display 38, scanning controller 30, reconstruction unit 36, R wave detecting unit 42, X-ray output control expert system 43, and X-ray output data storage unit 41. Although the reconstruction unit 36 corresponds to any of full reconstruction processing, half reconstruction processing, and segment reconstruction processing, the unit will be described as the one for half reconstruction processing. The R wave detecting unit 42 includes a function of typically detecting an R wave as a characteristic wave from the electrocardiogram data obtained by the electrocardiograph 22, and a function of repeatedly measuring the heart rate of the subject P on the basis of the period of the R wave.

The X-ray output data storage unit 41 stores the X-ray output data generated by the reference X-ray detector 24, together with a time code.

The X-ray output control expert system 43 has a function of setting a specific period in a cardiac cycle of a subject in time (msec) expression in accordance with a cardiac phase to be subjected to image reconstruction which is designated in percent expression by the operator through the input device 39, a function of performing extension processing for this specific period on the basis of a time width (time resolution) corresponding to the angle range of projection data required for image reconstruction and the rise time of X-rays, and a function of supplying data in the specific period having undergone the extension processing to the scanning controller 30. The scanning controller 30 executes ECG gated scanning on the basis of the data in the specific period having undergone the extension processing. That is, X-rays are generated from the X-ray tube 10 with reference to the R wave of the electrocardiogram, and the generation of X-rays is stopped in a period other than the specific period. Alternatively, the X-ray tube 10 generates X-rays at a relatively high intensity in the specific period with reference to the R wave of the electrocardiogram and generates X-rays at a relatively low intensity in a period other than the specific period. The generation/stop of X-rays or the modulation of X-rays is controlled by either a tube voltage or a filament current or a combination thereof. Control of the modulation of X-rays will be exemplified. In a period except for the specific period, a generation of X-rays may be stopped Note that the above rise time of X-rays is defined as the time required for the intensity of X-rays to reach from an almost zero value to, for example, 90% of a predetermined intensity value (relatively high output value) or the time required for the intensity of X-rays to reach from a predetermined relatively low intensity value to, for example, 90% of a predetermined intensity value (relatively high output value). The latter will be exemplified here.

Figure 7:
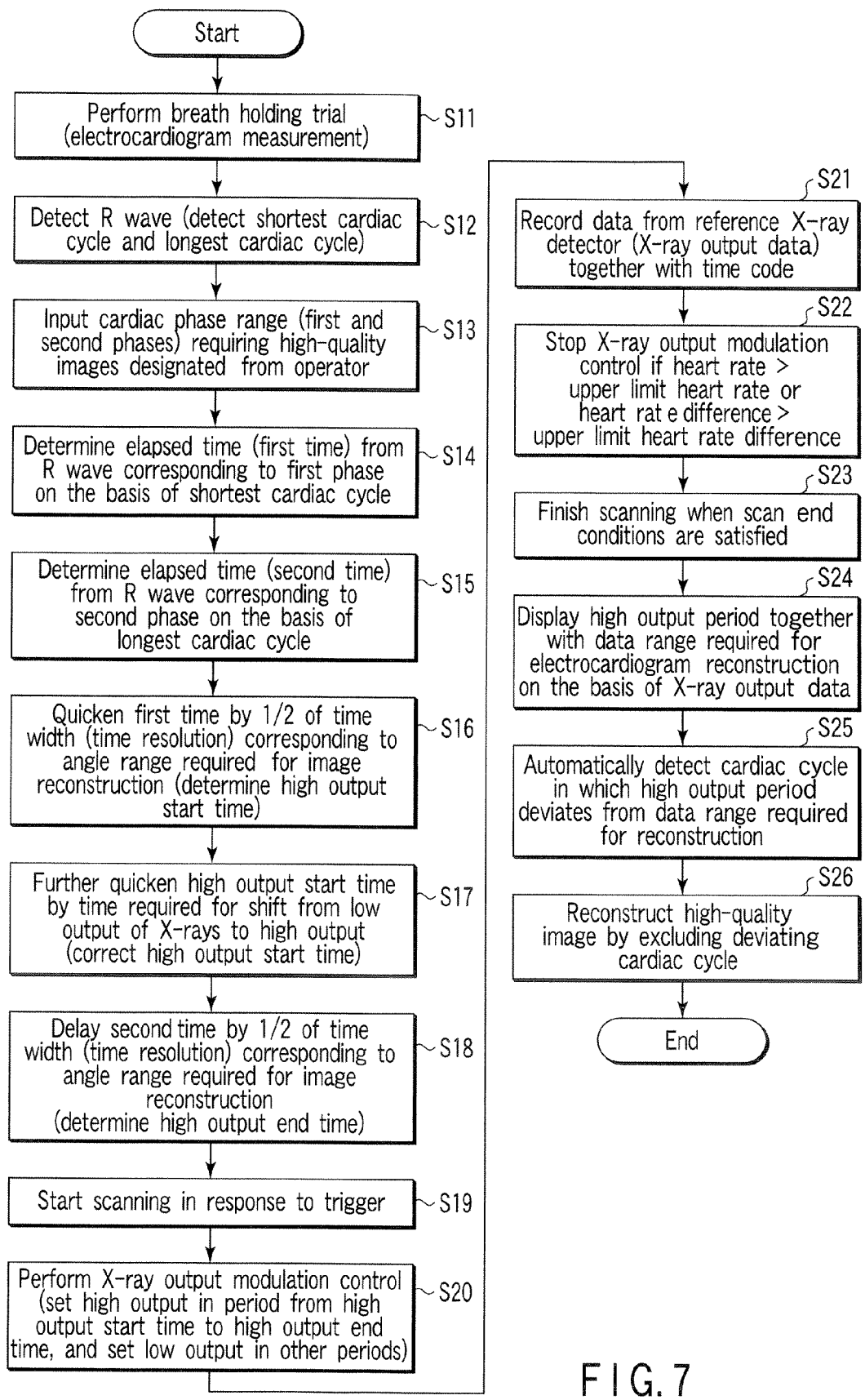
FIG. 7 is a flowchart showing sequences for scanning and processing before and after the scanning in this embodiment.

As shown in FIG. 7, the subject executes a breath holding trial (exercise) in a preparatory stage before scanning (S11) under the control of the system controller 29. An electrocardiogram in a period including at least the breath holding trial period is measured by the electrocardiograph 22. An R wave is detected by the R wave detecting unit 42 on the basis of the electrocardiogram (S12). The R wave detecting unit 42 detects an R wave and measures the interval between R waves as a cardiac cycle to specify a shortest cardiac cycle and a longest cardiac cycle in the breath holding trial period. The electrocardiogram is displayed on the display 38 as shown in FIG. 9. On this window, at least two cardiac phases, i.e., the first and second cardiac phases, are designated through the input device 39 (S13). The period from the first cardiac phase to the second cardiac phase is a period in which it is desired to acquire projection data with a high S/N ratio and perform image reconstruction with high image quality. Typically, a cardiac phase is designated in percentage (%) with the overall period of a single cardiac cycle being regarded as 100%. For example, 30% and 80% are designated.

Figure 8:
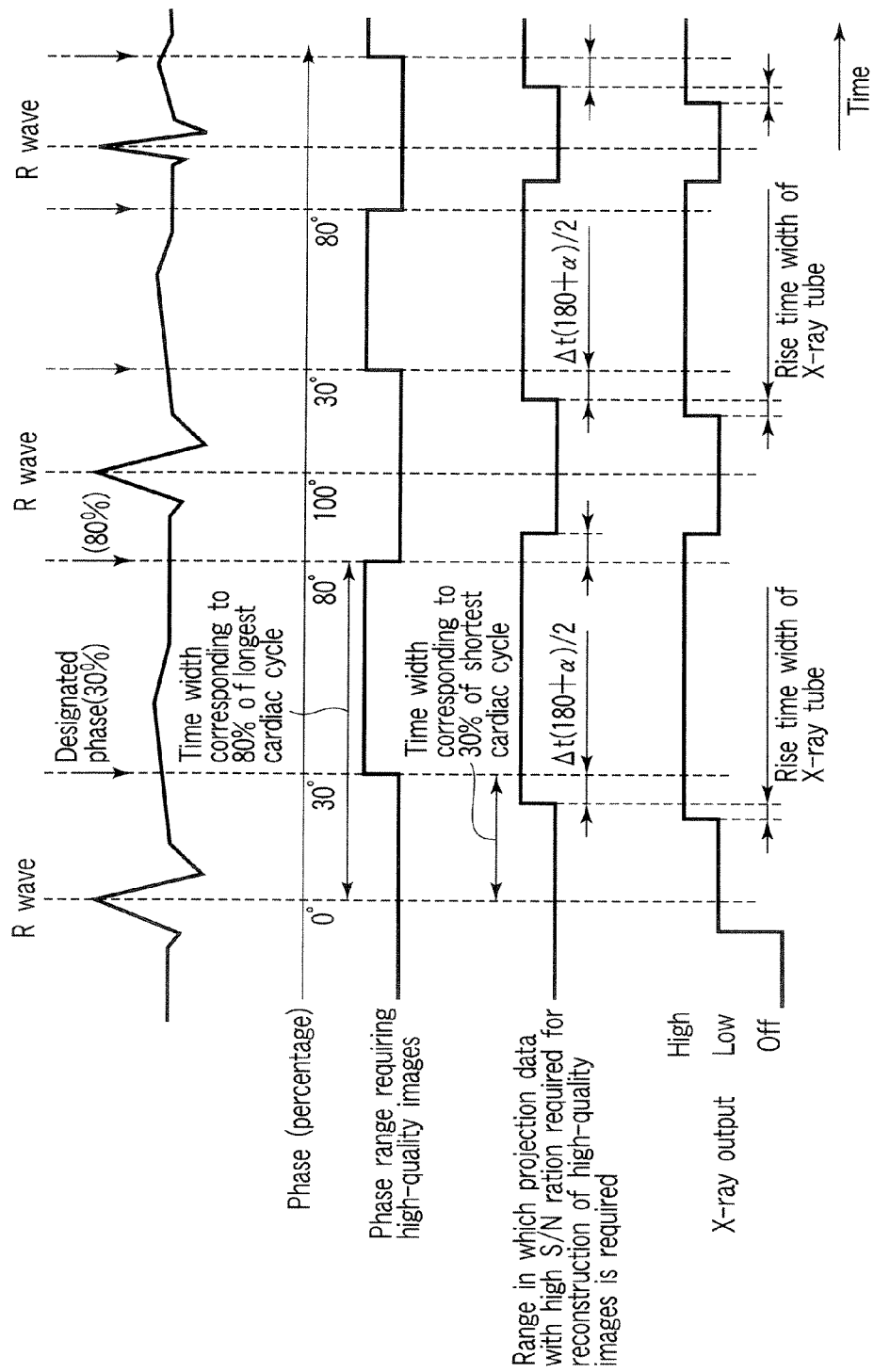
FIG. 8 is a timing chart for supplementary explanation of the flowchart of FIG. 7.

The X-ray output control expert system 43 converts the period designated in percentage into an elapsed time (msec) from the R wave. As shown in FIG. 8, first of all, the elapsed time (to be referred to as the first time) from the R wave which corresponds to the first cardiac phase (e.g., 30%) is determined from the shortest cardiac cycle (S14). The elapsed time (to be referred to as the second time) from the R wave which corresponds to the second cardiac phase (e.g., 80%) is determined from the longest cardiac cycle (S15).

The X-ray output control expert system 43 then quickens the start point (first time) of the period (specific period) from the first time to the second time which is expressed in msec and in which it is desired to perform image reconstruction with high image quality by ½ a time (time resolution) "Δt (180+α) required to reconstruct one-slice tomogram data, i.e., the time required for the X-ray tube 10 to rotate through (180°+α) (S16). The X-ray output control expert system 43 further quickens the first time by a predetermined rise time of X-rays (S17).

Likewise, the X-ray output control expert system 43 delays the end point (second time) of the period (specific period) from the first time to the second time which is expressed in msec and in which it is desired to perform image reconstruction with high image quality by a time corresponding to ½ the time resolution "Δt(180+α)" (S18).

In this manner, the start point and end point of a specific period are determined from the shortest cardiac cycle and longest cardiac cycle, respectively, and the specific period is extended on the basis of time resolution and the rise time of X-rays. This makes it possible to reduce the occurrence of a situation in which in ECG gated scanning, projection data required for image reconstruction of a desired cardiac phase has not been acquired or projection data has not been acquired with a relatively high S/N ratio.

As shown in FIG. 9, the X-ray output control expert system 43 displays, on the same time axis on the electrocardiogram in a breath holding trial period, the period (the data range required for reconstruction) from the first time determined in step S16 to the second time determined in step S18 and the period (expected X-ray high output period) from the first time determined in step S17 to the second time determined in step S18. The former period is a period required for high-quality images, and the latter period is an expected period in which X-rays are output at a high intensity. The operator can check the mismatch between the two periods on a window. The operator can extend or shorten the expected period in which X-rays are output at a high intensity, as needed, by operating the input device 39. Note that a period (a range in which high-quality images are required) specified by the percentage designated from the electrocardiogram of the subject or a specific waveform sequence may be displayed instead of the period (data range required for reconstruction) from the first time determined in step S16 to the second time determined in step S18.

The X-ray output control expert system 43 supplies data associated with the period from the first time to the second time which is determined by the X-ray output control expert system 43 to the scanning controller 30. The scanning controller 30 starts ECG gated scanning upon operation of a trigger button mounted on the input device 39 (S19).

The scanning controller 30 performs X-ray modulation control during ECG gated scanning. The scanning controller 30 modulates X-rays from low output to high output when a predetermined period of time has elapsed from the R wave pulse detected by the R wave detecting unit 42 and the first time is reached, and continues the high output state when a predetermined period of time has elapsed from the R wave pulse and the second time is reached. The scanning controller 30 modulates X-rays from high output to low output when a predetermined period of time has elapsed from the R wave pulse detected by the R wave detecting unit 42 and the second time is reached. Such X-ray output modulation control is repeated for each cardiac cycle.

The projection data acquired by the data acquisition device 26 during the continued ECG gated scanning period is sent to the projection data storage device 37 of the computer system 3 and stored, together with a time code. The electrocardiogram data obtained by the electrocardiograph 22 is also stored in the projection data storage device 37. In addition, the X-ray output data generated by the reference X-ray detector 24 is stored in the X-ray output data storage unit 41, together with a time code (S21).

Assume that during an ECG gated scanning period, when the heart rate of the subject exceeds a predetermined upper heart rate, or the heart rate in the last cardiac cycle becomes higher than the heart rate in the immediately preceding cardiac cycle and their difference exceeds a predetermined upper limit heart rate difference (e.g., 19 ppm), i.e., the last cardiac cycle becomes extremely shorter than the immediately preceding cardiac cycle, the scanning controller 30 stops subsequent X-ray output modulation control (S22). Assume that as shown in FIG. 10, the heart rate in a cardiac cycle Sn immediately before the current time is 48, the heart rate in an immediately preceding cardiac cycle Sn−1 is 68, and their heart rate difference "20" exceeds the upper limit heart rate difference "19". In this case, X-ray output modulation control is stopped from a subsequent cardiac cycle Sn+1, and X-rays are steadily maintained at a high output level. This stop control can prevent data omission even if arrhythmia occurs.

When a predetermined scanning termination condition, e.g., the lapse of a predetermined period of time from breath holding, is satisfied, the scanning is terminated (S23).

Figure 11:
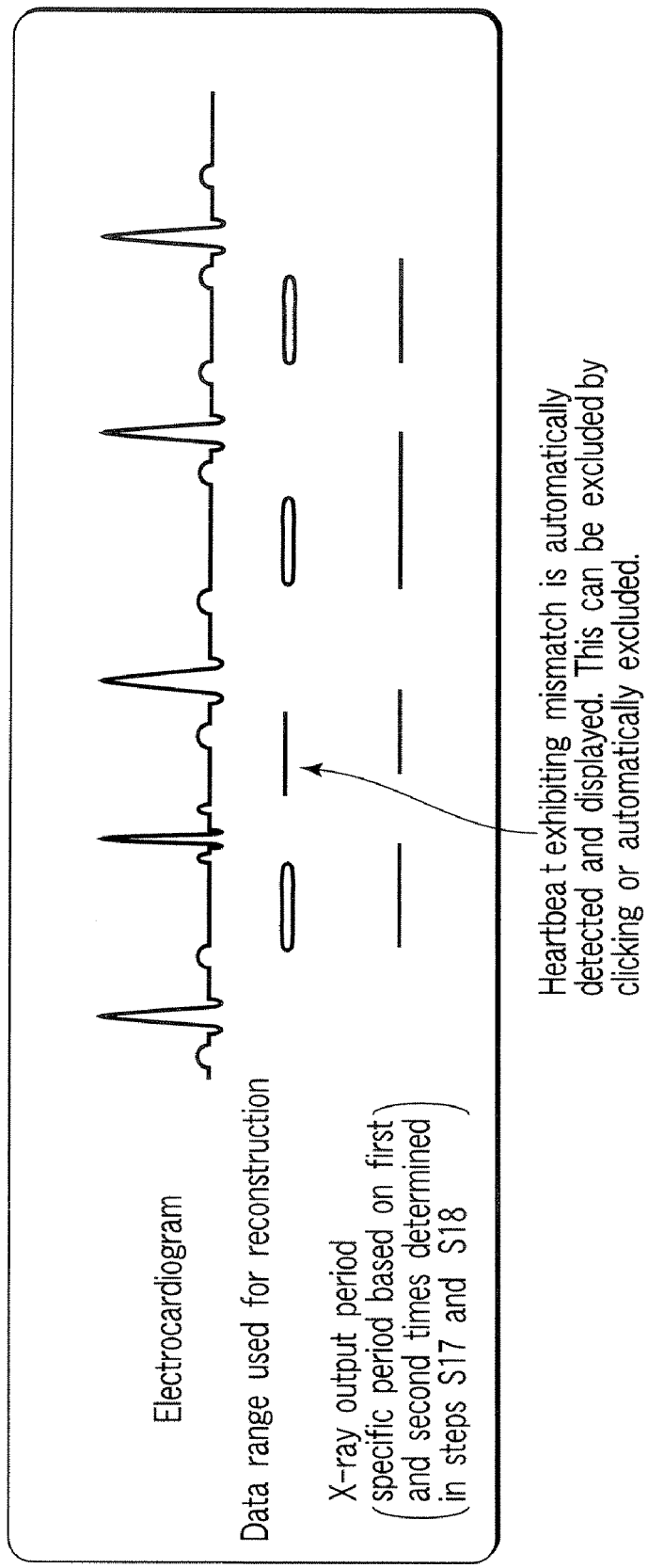
FIG. 11 is a view showing an example of a check window to be displayed by the X-ray output control expert system in FIG. 5 in step S24 after the end of scanning.

As shown in FIG. 11, after the scanning, the X-ray output control expert system 43 displays the electrocardiographic data stored in the projection data storage device 37, and displays, on the same time axis in accordance with a time code, the period (the data range required for reconstruction) from the first time determined in step S16 to the second time determined in step S18 and the period (the period in which high image quality is maintained) which is specified on the basis of the X-ray output data stored in the X-ray output data storage unit 41 in step S21 and in which X-rays are actually output at a high output level (S24). Note that the X-ray output control expert system 43 may display the period (the range in which high-quality images are required) specified by the percentage designated from an electrocardiogram of the subject or a specific waveform sequence instead of the period (the data range required for reconstruction) from the first time determined in step S16 to the second time determined in step S18.

The X-ray output control expert system 43 automatically detects that a cardiac cycle which is specified for each cardiac cycle from the percentage designated in step S13 and in which a high-quality image is desired deviates at least partly from the X-ray high output period (the period in which high image quality is maintained) which is specified on the basis of the X-ray output data stored in the X-ray output data storage unit 41 in step S21 (S25). Alternatively, the operator can determine the corresponding cardiac cycle and automatically designate it. The reconstruction unit 36 excludes projection data acquired in the detected cardiac cycle, and performs image reconstruction (S26).

This embodiment can reduce the occurrence of a situation in which projection data required for image reconstruction of a desired cardiac phase has not been acquired or projection data has not been acquired with an expected relatively high S/N ratio.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray source which generates X-rays;
   an X-ray detector which detects X-rays transmitted through a subject to be examined to generate projection data;
   a storage unit which stores the projection data in association with electrocardiographic data of the subject;
   a setting unit which sets a specific cardiac phase in accordance with an operator's instruction;
   a reconstruction unit which reconstructs an image on the basis of a plurality of projection data sets acquired in a plurality of specific periods throughout a plurality of cardiac cycles;
   a determining unit which determines a first period in which the subject is scanned by a high dose of X-rays in the cardiac cycles of the subject in order to include the specific cardiac phase even if a heart rate of the subject varies within a fluctuation range of the heart rate; and
   a control unit which controls a tube current of the X-ray source to generate a relatively high dose of X-rays in the first period and generate a relatively low dose of X-rays or stop a generation of X-rays in a second period other than the first period.

2. An apparatus according to claim 1, wherein the heart rate fluctuation range is determined on the basis of a heart rate corresponding to a plurality of heartbeats.

3. An apparatus according to claim 1, wherein the heart rate fluctuation range is determined in accordance with an operator's instruction.

4. An apparatus according to claim 3, further comprising a display unit which displays a graph representing a temporal change in heart rate before the scanning; and
   an operation unit to designate a heart rate fluctuation range on the graph.

5. An apparatus according to claim 4, wherein the display unit displays a graph indicating a relationship between a partial time including at least one of a maximum heart rate and a minimum heart rate, and an electrocardiogram in a period corresponding to the graph.

6. An apparatus according to claim 1, wherein the heart rate fluctuation range is determined on the basis of a typical value of a plurality of heart rates obtained before acquisition of the projection data.

7. An apparatus according to claim 1, wherein the heart rate fluctuation range is determined to a range of a maximum heart rate and a minimum heart rate in a breathing exercise period.

8. An apparatus according to claim 7, wherein the determining unit determines an extended period by extending each of the specific periods on the basis of the heart rate fluctuation range of the subject; and
   a start point of the extended period is set to a start point of a period corresponding to the maximum heart rate, and an end point of the extended period is set to an end point of a period corresponding to the minimum heart rate.

9. An apparatus according to claim 8, wherein the control unit controls a tube current of the X-ray source to modulate a tube current to be supplied from the high voltage generating unit to the X-ray source in the extended specific period and said second period.

10. An apparatus according to claim 9, wherein the control unit determines a tube current value in the specific period in accordance with an operator's instruction, and determines a tube current value in said second period on the basis of the tube current value in the specific period.

11. An apparatus according to claim 9, wherein the control unit provides, between the specific period and said second period, a transition period of a tube current value between the tube current value in the specific period and the tube current value in said second period.

12. An apparatus according to claim 1, wherein the specific cardiac phase and a heart rate fluctuation range are converted into delay times with reference to an R wave, and the control unit controls the tube current of the X-ray source with the converted delay times.

13. An apparatus according to claim 1, wherein the control unit controls the tube current to generate the high dose of the X-rays in said second period when a heart rate obtained in parallel with acquisition of the projection data deviates from the heart rate fluctuation range.

14. An apparatus according to claim 1, wherein the control unit controls the high voltage generating unit to change a tube current value in said second period within a range of a tube current value in the specific period and a tube current value in a pre-scanning period when pre-scanning is performed to obtain a contrast medium injection timing before acquisition of the projection data.

15. An apparatus according to claim 1, wherein the reconstruction unit weights and adds projection data with the same view between said plurality of projection data sets.

16. An apparatus according to claim 15, wherein the reconstruction unit applies, to the projection data with the same view, a weight corresponding to a heart rate in a cardiac cycle in which the projection data are acquired.

17. An apparatus according to claim 16, wherein a weight applied to projection data acquired in a cardiac cycle in which the heart rate is relatively high is lower than a weight applied to projection data acquired in a cardiac cycle in which the heart rate is relatively low.

18. An apparatus according to claim 15, wherein the reconstruction unit applies, to the projection data with the same view, a weight corresponding to an occupation ratio of said each projection data set to an angle range required for image reconstruction.

19. An apparatus according to claim 18, wherein a weight to be applied to projection data in a projection data set which is relatively high in the ratio is heavier than a weight to be applied to projection data in a projection data set which is relatively low in the ratio.

20. An apparatus according to claim 1, wherein the projection data are acquired by helical scanning, and the reconstruction unit sequentially reconstructs tomograms by real-time reconstruction on the basis of at least part of projection data obtained by the X-ray detector in parallel with the helical scanning, and reconstructs an image by cone beam reconstruction on the basis of projection data after the end of the helical scanning.

21. An apparatus according to claim 1, wherein said fluctuation range is determined as a heart rate range about an average heart rate over the plurality of cardiac cycles.

22. An apparatus according to claim 21 wherein the heart rate range is 20-30 heart beats per minute centered about the average heart rate.

23. An apparatus according to claim 1, wherein the determining unit determines the first period by adjusting the specific cardiac phase using the heart rate fluctuation range of the subject.

24. An X-ray computed tomography apparatus comprising:
a storage unit which stores electrocardiographic information acquired from a subject to be examined to be examined;
a setting unit which sets a cardiac phase of the subject which is to be reconstructed; an X-ray source which applies X-rays to the subject;
an X-ray detector which detects X-rays transmitted through the subject; a reconstruction unit which reconstructs an image of a cardiac phase set by the setting unit on the basis of projection data detected by the detector; and
a control unit which controls a tube current of the X-ray source to scan, at a high X-ray dose, a first period obtained by adding a margin period to a period required for reconstruction of the cardiac phase set by the setting unit, and to scan at a low X-ray dose or to stop a generation of X-rays in the second period.

25. An X-ray computed tomography apparatus comprising:
a gantry which includes an X-ray source which applies X-rays to a subject to be examined and an X-ray detector which detects X-rays transmitted through the subject, and scans the subject;
a storage unit which stores an electrocardiogram acquired from the subject;
a displaying unit which displays said electrocardiogram along with a graph of corresponding heart rates;
a setting unit which permits an operator to set a cardiac phase range in which a tomogram of the subject is reconstructed;
a reconstruction unit which reconstructs a tomogram of a specific phase in a cardiac phase range set by the setting unit on the basis of projection data detected by the detector; and
a control unit which controls a tube current of the X-ray source to scan in the cardiac phase range set by the setting unit at a high X-ray dose and scan at a low X-ray dose or stop a generation of X-rays in a range obtained by excluding the cardiac phase range, from the electrocardiographic cycle in response to an electrocardiogram as a trigger which is obtained in parallel with the scanning.

26. An apparatus according to claim 25, wherein:
the display unit displays an initial heart rate fluctuation range; and
setting unit modifies the initial heart rate fluctuation range to produce the cardiac phase range.

27. An X-ray computed tomography apparatus comprising:
a scanning unit which includes an X-ray source which applies X-rays to a subject to be examined and an X-ray detector which detects X-rays transmitted through the subject, and scans the subject;
a storage unit which stores an electrocardiogram acquired from the subject in parallel with the scanning;
a setting unit which sets a cardiac phase range in which an image of the subject is reconstructed having a starting point determined using a maximum heart rate in a plurality of cardiac cycles in the electrocardiogram and having an end point determined using a minimum heart rate in the plurality of cardiac cycles in the electrocardiogram;
a reconstruction unit which reconstructs an image of a cardiac phase set by the setting unit on the basis of projection data detected by the detector; and
a control unit which controls a tube current of the X-ray source to increase an X-ray dose in a predetermined range including a cardiac phase set by the setting unit and decrease an X-ray dose or stop a generation of X-rays in a range excluding the predetermined range on the basis of an electrocardiogram acquired in parallel with the scanning.

28. An apparatus according to claim 27, wherein the control unit controls the high voltage generating unit to prevent an X-ray dose in a range excluding the predetermined range from decreasing below a predetermined value.

29. An apparatus as recited in claim 27, wherein the maximum and minimum heart rates are determined in the second plurality of cardiac cycles after at least one of omitting a number of heart rates from the second plurality of cardiac cycles.

30. An X-ray computed tomography apparatus comprising:
a scanning unit which includes an X-ray source which applies X-rays to a subject to be examined and an X-ray detector which detects X-rays transmitted through the subject, and scans the subject;
a storage unit which stores electrocardiographic information acquired from the subject before the scanning and in parallel with the scanning;
a displaying unit which displays said electrocardiogram along with a graph of corresponding heart rates;
a setting unit which sets a cardiac phase in which an image of the subject is to be reconstructed;
a reconstruction unit which reconstructs an image of a cardiac phase set by the setting unit on the basis of projection data detected by the detector; and a control unit which controls a tube current of the X-ray source to increase an X-ray dose in a predetermined range determined on the basis of a plurality of heart rates acquired before the scanning which are stored in the storage unit and decrease an X-ray dose or stop a generation of X-rays in a range excluding the predetermined range in response to electrocardiographic information as a trigger which is obtained in parallel with the scanning and stored in the storage unit.

31. An X-ray computed tomography apparatus comprising:

an X-ray source which generates X-rays; an X-ray detector which detects X-rays transmitted through a subject to be examined to generate projection data;

a specific period setting unit which sets a specific period in a cardiac cycle of the subject in accordance with an operator's instruction;

a reconstruction unit which reconstructs an image on the basis of projection data acquired in the specific period;

an extension processing unit which determines an extended period by extending the specific period on the basis of a time width corresponding to an angle range of projection data required for image reconstruction; and a control unit which controls generation/stop or intensity modulation of X-rays from the X-ray tube in accordance with the extended specific period.

32. An apparatus according to claim 31, wherein an X-ray intensity in the extended specific period is higher than an X-ray intensity in a period other than the extended specific period.

33. A n apparatus according to claim 31, wherein X-rays are generated in the extended specific period, and generation of X-rays is stopped in a period other than the extended specific period.

34. An apparatus according to claim 31, wherein each of a start and end of the specific period is extended by ½ of a time width corresponding to an angle range of projection data required for the image reconstruction.

35. An apparatus according to claim 34, wherein a start of the specific period is advanced by one of a rise time of the X-rays and a time corresponding to the rise time upon one of generation and modulation of the X-rays in addition to a time corresponding to ½ of a time width corresponding to the angle range of the projection data required for the image reconstruction.

36. An apparatus according to claim 31, wherein the time width corresponding to the angle range of the project data required for the image reconstruction is a time required for the X-ray tube to rotate through (180°+fan angle) corresponding to a half reconstruction method.

37. An apparatus according to claim 31, wherein a start of the specific period is determined on the basis of a shortest time of a plurality of cardiac cycles acquired in advance from the subject, and an end of the specific period is determined on the basis of a longest time of the plurality of cardiac cycles acquired in advance from the subject.

38. An apparatus according to claim 31, wherein a start and end of the specific period are set as elapsed times from a specific waveform of the electrocardiogram.

39. An apparatus according to claim 31, wherein the specific period setting means converts a start and end of the specific period designated by the operator in percentage when the entire cardiac cycle is regarded as 100% into elapsed times from a specific waveform of the electrocardiogram.

40. An apparatus according to claim 39, further comprising a measuring unit which measures one of an output from the X-ray tube and a signal reflecting the output, and a storage unit which stores data of an output from the measuring unit, together with information which can be made to correspond to a time.

41. An apparatus according to claim 40, further comprising means for displaying one of an electrocardiogram of the subject and a sequence of the specific waveform, together with a data range used for reconstruction corresponding to the designated percentage and a period which is specified from the stored data of the output from the measuring unit and in which the X-rays are generated or a high intensity thereof is maintained.

42. An apparatus according to claim 41, wherein projection data acquired in a cardiac cycle in which the data range used for the reconstruction is excluded from a period which is specified from the stored data of the output from the measuring unit and in which the X-rays are generated or a high intensity thereof is maintained is excluded from image reconstruction processing.

43. An apparatus according to claim 42, further comprising designation means which is used by an operator to designate a cardiac cycle in which the data range used for the reconstruction is excluded from a period which is specified from the stored data of the output from the measuring unit and in which the X-rays are generated or a high intensity thereof is maintained.

44. An apparatus according to claim 42, further comprising means for automatically extracting a cardiac cycle in which the data range used for the reconstruction is excluded from a period which is specified from the stored data of the output from the measuring unit and in which the X-rays are generated or a high intensity thereof is maintained.

45. An apparatus according to claim 40, further comprising means for displaying one of an electrocardiogram of the subject and a sequence of the specific waveform, together with a period specified by the designated percentage from said one of the electrocardiogram of the subject and the sequence of the specific waveform, and a period which is specified from the stored data of the output from the measuring unit and in which the X-rays are generated or a high intensity thereof is maintained.

46. An apparatus according to claim 31, wherein when a heart rate of the subject exceeds a predetermined upper limit rate, the control unit stops control on generation/stop or intensity modulation of the X-rays.

47. An apparatus according to claim 31, wherein when a fluctuation in heart rate of the subject exceeds a predetermined upper limit rate, the control unit stops control on one of generation/stop and intensity modulation of the X-rays.

48. An X-ray computed tomography apparatus comprising:

an X-ray source which generates X-rays;

an X-ray detector which detects X-rays transmitted through a subject to be examined to generate projection data;

a storage unit which stores the projection data in association with electrocardiographic data of the subject;

a setting unit which sets a specific cardiac phase in accordance with an operator's instruction;

a reconstruction unit which reconstructs an image on the basis of a plurality of projection data sets acquired in a plurality of specific periods throughout a first plurality of cardiac cycles, the specific periods corresponding the specific cardiac phase;

a period extending unit which extends each of the specific periods on the basis of a heart rate fluctuation range of the subject over a second plurality of cardiac cycles in the electrocardiogram; and a control unit which controls a tube current of the X-ray source to generate a relatively high dose of X-rays and generate a relatively low dose of X-rays or stop a generation of X-rays in a period other than the extended specific period, wherein the period extending unit modifies a start point of the specific period using a shortest cardiac cycle in the plurality of cardiac cycles and modifies and end point of the specific period using a longest cardiac cycle in the second plurality of cardiac cycles.

49. An X-ray computed tomography apparatus comprising:

a gantry which includes an X-ray source which applies X-rays to a subject to be examined and an X-ray detector which detects X-rays transmitted through the subject, and scans the subject;

a storage unit which stores an electrocardiogram acquired from the subject;

a displaying unit which displays said electrocardiogram and indicates corresponding periods of data reconstruction and periods of X-ray exposure;

a setting unit which permits adjustment of the periods of X-ray exposure;

a reconstruction unit which reconstructs a tomogram based upon data obtained by scanning in the periods of X-ray exposure; and a control unit which controls the X-ray source to scan in the periods of X-ray exposure set by the setting unit at a first X-ray dose sufficient to produce said data and scan in periods other than said periods of X-ray exposure at a second X-ray dose lower than the first X-ray dose or with generation of X-rays inhibited.

* * * * *